US012674125B2

(12) United States Patent　　　　(10) Patent No.:　US 12,674,125 B2
Grangier et al.　　　　　　　　　　(45) Date of Patent:　Jul. 7, 2026

(54) FLUIDIC SYSTEM FOR PRODUCING EXTRACELLULAR VESICLES AND ASSOCIATED METHOD

(71) Applicants: CENTRE NATIONAL DE LA RECHERCHE SCIENTIFIQUE, Paris (FR); UNIVERSITÉ DE PARIS, Paris (FR)

(72) Inventors: Alice Grangier, Gentilly (FR); Amanda Silva, Igny (FR); Florence Gazeau, Le Kremlin-Bicêtre (FR); Claire Wilhelm, Vélizy-Villacoublay (FR); Max Piffoux, Paris (FR); François Heslot, Viroflay (FR)

(73) Assignees: CENTRE NATIONAL DE LA RECHERCHE SCIENTIFIQUE, Paris (FR); UNIVERSITÉ DE PARIS, Paris (FR)

( * ) Notice: Subject to any disclaimer, the term of this patent is extended or adjusted under 35 U.S.C. 154(b) by 1090 days.

(21) Appl. No.: 17/418,970

(22) PCT Filed: Dec. 27, 2019

(86) PCT No.: PCT/FR2019/053309
　　§ 371 (c)(1),
　　(2) Date: Jun. 28, 2021

(87) PCT Pub. No.: WO2020/136362
　　PCT Pub. Date: Jul. 2, 2020

(65) Prior Publication Data
　　US 2022/0119748 A1　　Apr. 21, 2022

(30) Foreign Application Priority Data

Dec. 28, 2018　(FR) ..................................... 1874295

(51) Int. Cl.
　　*C12M 3/06*　　　(2006.01)
　　*C12M 1/00*　　　(2006.01)
　　　　(Continued)

(52) U.S. Cl.
　　CPC ............ *C12M 23/16* (2013.01); *C12M 23/34* (2013.01); *C12M 27/02* (2013.01); *C12M 29/04* (2013.01);
　　　　(Continued)

(58) Field of Classification Search
　　None
　　See application file for complete search history.

(56) References Cited

U.S. PATENT DOCUMENTS 4,806,484 A　　2/1989　Petrossian et al.
5,447,853 A　　9/1995　Tokashiki et al.
　　　　(Continued)

FOREIGN PATENT DOCUMENTS

CN　　109071597 A　　12/2018
EP　　　1705243 A1　　9/2006
　　　　(Continued)

OTHER PUBLICATIONS

Haraszti et al., "Exosomes Produced From 3D Cultures Cultures of MSCS by Tangential Flow Filtration Show Higher Yield and Improved Activity", Molecular Therapy, vol. 26, No. 12, Dec. 2018, pp. 2838-2847.
　　　　(Continued)

*Primary Examiner* — William H. Beisner
(74) *Attorney, Agent, or Firm* — Maier & Maier, PLLC

(57)　　　ABSTRACT

A fluidic system for producing extracellular vesicles from suspended producer cells, including at least one container, a liquid medium contained in the container, suspended producer cells, a liquid medium agitator, a device for controlling the speed of the agitator suitable for the growth of the
　　　　(Continued)

suspended producer cells, wherein the device for controlling the speed of the agitator, the agitator and the shape and dimensions of the container are suitable for generating a turbulent flow of the liquid medium in the container for exerting shear stresses on the producer cells in order to carry out the production of extracellular vesicles, the Kolmogorov length of the flow being less than or equal to 50 μm.

9 Claims, 9 Drawing Sheets

(51) Int. Cl.
| | |
|---|---|
| *C12M 1/06* | (2006.01) |
| *C12N 5/0781* | (2010.01) |
| *C12N 5/09* | (2010.01) |

(52) U.S. Cl.
CPC ......... *C12N 5/0635* (2013.01); *C12N 5/0693* (2013.01); *C12N 2527/00* (2013.01)

(56) References Cited

U.S. PATENT DOCUMENTS

| | | | | |
|---|---|---|---|---|
| 12,098,355 | B2 * | 9/2024 | Gazeau | ................... C12M 27/14 |
| 2009/0143993 | A1 | 6/2009 | Cales | |
| 2010/0160183 | A1 | 6/2010 | Xu et al. | |
| 2012/0045834 | A1 | 2/2012 | Jones et al. | |
| 2015/0166948 | A1 | 6/2015 | Dehottay et al. | |
| 2016/0331686 | A1 | 11/2016 | Polach et al. | |
| 2016/0355776 | A1 * | 12/2016 | Lipkens | ................. C12M 35/04 |
| 2017/0137774 | A1 | 5/2017 | Lipkens et al. | |
| 2018/0193263 | A1 | 7/2018 | Muraca et al. | |
| 2019/0175506 | A1 | 6/2019 | Noyes et al. | |
| 2020/0155703 | A1 | 5/2020 | Lôtvall et al. | |
| 2020/0385665 | A1 | 12/2020 | Gazeau et al. | |

FOREIGN PATENT DOCUMENTS

| | | | |
|---|---|---|---|
| EP | 2749635 | A2 | 7/2014 |
| GB | 2163453 | A | 2/1986 |
| JP | 2006296423 | A | 11/2006 |
| JP | 2020528763 | A | 10/2020 |
| WO | 03002590 | A2 | 1/2003 |
| WO | 2004083379 | A2 | 9/2004 |
| WO | 2015048566 | A1 | 4/2015 |
| WO | 2016168680 | A1 | 10/2016 |
| WO | 2017075465 | A1 | 5/2017 |
| WO | 2017076924 | A1 | 5/2017 |
| WO | 2017117585 | A1 | 7/2017 |
| WO | 2017193075 | A1 | 11/2017 |
| WO | 2018102608 | A1 | 6/2018 |
| WO | 2019060629 | A1 | 3/2019 |
| WO | 2019213706 | A1 | 11/2019 |
| WO | 2020136361 | A1 | 7/2020 |

OTHER PUBLICATIONS

International Search Report issued on May 13, 2020 in corresponding International Application No. PCT/FR2019/053309; 6 pages.

Haney Matthew J et al. "Exosomes as drug delivery vehicles for Parkinson's disease therapy" Journal of Controlled Release, Elsevier, Amsterdam, NL, vol. 207, Mar. 31, 2015 (Mar. 31, 2015), pp. 18-30, 14 pgs.

Kolmogorov, A. N., 1941, January, "The local structure of turbulence in incompressible viscous fluid for very large Reynolds numbers", In Dokl. Akad. Nauk, SSSR, vol. 30, No. 4, pp. 301-305, 6 pgs.

Nienow, A. W., & Miles, D., 1971, "Impeller power Nos. in closed vessels", Industrial & Engineering Chemistry Process Design and Development, 10(1), 41-43, 3 pgs.

Piffoux, M., Silva, A. K., Lugagne, J. B., Hersen, P., Wilhelm, C., & Gazeau, F., 2017, "Extracellular Vesicle Production Loaded with Nanoparticles and Drugs in a Trade-off between Loading, Yield and Purity: Towards a Personalized Drug Delivery System", Advanced Biosystems, 12 pgs.

Watson, D. C., Bayik, D., Srivatsan, A., Bergamaschi, C., Valentin, A., Niu, G., . . . & ~Jones, J. C., 2016, "Efficient production and enhanced tumor delivery of engineered extracellular vesicles", Biomaterials, 105, 195-205, 27 pgs.

Zhou, G., Kresta, S. M., 1996, "Impact of tank geometry on the maximum turbulence energy dissipation rate for mpellers", AlChE journal, 42(9), 2476-2490, 15 pgs.

Alvarez-Erviti et al., "Delivery of siRNA to the mouse brain by systemic injection of targeted exosomes", Nature Biotechnology, Nov. 28, 2011, vol. 29, No. 4, pp. 341-347.

Farjadian et al., "Nanopharmaceuticals and nanomedicines currently on the market: challenges and opportunities", Nanomedicine (Lond.), Jan. 2019, vol. 14, No. 1, pp. 93-126.

Lamichhane et al., "Exogenous DNA Loading into Extracellular Vesicles via Electroporation is Size-Dependent and Enables Limited Gene Delivery", Mol Pharm, Oct. 5, 2015, vol. 12, No. 10, 21 pages.

Shtam et al., "Exosomes are natural carriers of exogenous siRNA to human cells in vitro", Cell Communication and Signaling, Nov. 18, 2013, vol. 11, No. 88, 10 pages.

Smyth et al., "Surface Functionalization of Exosomes Using Click Chemistry", Bioconjugate Chemistry, Oct. 15, 2014, vol. 25, No. 10, pp. 1777-1784.

Strohl, "Fusion Proteins for Half-Life Extension of Biologics as a Strategy to Make Biobetters", BioDrugs, 2015, vol. 29, No. 4, pp. 215-239.

Tian et al., A doxorubicin delivery platform using engineered natural membrane vesicle exosomes for targeted tumor therapy, Biomaterials, Feb. 2014, vol. 35, No. 7, pp. 2383-2890.

Thery et al., "Minimal information for studies of extracellular vesicles 2018 (MISEV2018): a position statement of the International Society for Extracellular Vesicles and update of the MISEV2014 guidelines", Journal of Extracellular Vesicles, 2018, vol. 7, No. 1, 43 pages.

Whitehead et al., "Knocking down barriers: advances in siRNA delivery", Nature Reviews, Drug Discovery, 2009, vol. 8, No. 2, pp. 129-139.

El Andaloussi et al., "Extracellular vesicles: biology and emerging therapeutic opportunities", Nature Reviews, Drug Discovery, 2013, vol. 12, pp. 347-357.

Enomura et al., "Development and Applicability of a New Mediales Disperser", Coloring Materials, vol. 75, No. 12, 2022, pp. 586-591 (English abstract provided).

Rani et al., "Mesenchymal Stem Cell-derived Extracellular Vesicles: Toward Cell-free Therapeutic Applications", Molecular Therapy, May 2015, vol. 23, No. 5, pp. 812-823.

Lee et al., "New paradigm of scalable manufacturing for allogeneic cell therapy products", Scale-up and Manufacturing of Cell-Based Therapies, ECI Symposium, 2017, retrieved from <URL: http://www.dc.engconfintl.org/cellbasedtherapies_v/62/>, 2 pages.

Teixeira et al., "Modulation of the Mesenchymal Stem Cell Secretome Using Computer-Controlled Bioreactors: Impact on Neuronal Cell Proliferation, Survival and Differentiation", Scientific Reports, Jun. 2016, vol. 6, No. 27791, 14 pages.

Ozturk et al., "An Approach for Assessing Turbulent Flow Damage to Blood in Medical Devices", Journal of Biomechanical Engineering, Jan. 2017, vol. 139, pp. 011008-1-011008-8.

Xu et al., "Motion of inertial particles with size larger than Kolmogorov scale in turbulent flows", Physica D: Nonlinear Phenomena, 2008, vol. 237, pp. 2095-2100.

Nienow et al., "Mixing Theory for Culture and Harvest in Bioreactors of Human Mesenchymal Stem Cells on Microcarriers", Theoretical Foundations of Chemical Engineering, Pleiades Publishing, Ltd., Dec. 2, 2016, vol. 50, No. 6, pp. 895-900.

Shimasaki et al., "Characteristics of Flotation, Sedimentation and Entrainment of Particle in Agitated Liquid", Tetsu-to-Hagane, 2003, vol. 89, No. 6, pp. 637-644.

(56) References Cited

OTHER PUBLICATIONS

Office Action issued on Sep. 3, 2025, in corresponding Mexican Application No. MX/a/2021/007776, 20 pages.

* cited by examiner

Agitation (rotations per minute)

FLUIDIC SYSTEM FOR PRODUCING EXTRACELLULAR VESICLES AND ASSOCIATED METHOD

FIELD

The invention relates generally to the production of extracellular vesicles. More specifically, the invention relates to a system for producing extracellular vesicles from suspended producer cells, a method for producing and recovering such vesicles and vesicles produced by such a system, the extracellular vesicles can for example be of interest as vectors of therapeutic and/or imaging agent, as an alternative to cell therapy and in regenerative medicine.

BACKGROUND

The cells are known to release extracellular vesicles in their environment, for example, in vivo, in the biological fluids of an organism. The extracellular vesicles have been identified as effective means for delivering drugs, in a personalized or targeted manner, into the human body. They first have a native biocompatibility and an immune tolerance. They can also internalize theranostic nanoparticles, making it possible both to image certain parts of the body and to deliver active ingredients having therapeutic functions. The extracellular vesicles also have a function of intercellular communication: they allow, for example, to transport lipids, membrane and cytoplasmic proteins and/or nucleotides of the cell cytoplasm, such as mRNAs, microRNAs or long non-coding RNAs, between different cells.

In particular, the use of extracellular vesicles can solve problems known in the therapeutic use of cells, such as cell replication, differentiation, vascular occlusions, risk of rejection and difficulties in storage and freezing. Therefore, there is an industrial need for the production of cell vesicles in amounts sufficient for therapeutic use, in particular in replacement or in addition to cell therapies.

For this purpose, Piffoux et al. (Piffoux, M., Silva, A. K., Lugagne, J. B., Hersen, P., Wilhelm, C., & Gazeau, F., 2017, *Extracellular Vesicle Production Loaded with Nanoparticles and Drugs in a Trade-off between Loading, Yield and Purity: Towards a Personalized Drug Delivery System*, Advanced Biosystems) describe the comparison of different methods for the production of extracellular vesicles.

A first method consists in producing extracellular vesicles from endothelial cells of the umbilical cord vein (HUVEC), by subjecting these cells to hydrodynamic stresses mimicking the stresses exerted under physiological conditions within the blood capillaries or under pathological conditions during stenosis of the blood vessels. These stresses are driven by the passage of the producer cells into microfluidic channels. A microfluidic chip comprises two hundred channels in which the cells are transported in a laminar flow, to produce vesicles in a parallelized manner.

However, this method has problems of dimensioning: the amounts of vesicles produced by a microfluidic chip are not suitable for the amounts required for the aforementioned applications. Moreover, the yield of extracellular vesicles produced per cell introduced into such a chip (about $2 \times 10^4$ vesicles per cell) is very lower than the theoretical maximum yield of vesicles produced by a cell, for example of the order of $3.5 \times 10^6$ vesicles per cell for a cell of the MSC type (Mesenchymal Stem Cell). Finally, this method requires compliance with the standards referred to as GMP (Good Manufacturing Practices), necessary for the manufacture of medicines.

A second method commonly used in the literature and described by Piffoux et al. consists in cultivating HUVEC in a culture medium of DMEM type (Dulbecco's Modified Eagle's Medium) without serum, for three days (starvation technique, or serum deficiency). The absence of serum results in cell stress triggering release of vesicles by the producer cells. This method has a higher yield and makes it possible to produce a greater quantity of vesicles than the method using a microfluidic chip (about $4 \times 10^4$ vesicles per producer cell). However, the calculated yield corresponds to a much longer production time than the production time of the preceding method. This method does not make it possible to produce an amount of extracellular vesicles sufficient for the aforementioned applications.

Finally, this method does not make it possible to produce vesicles continuously because it induces cell death.

Watson et al. (Watson, D. C., Bayik, D., Srivatsan, A., Bergamaschi, C., Valentin, A., Niu, G., . . . & Jones, J. C., 2016, *Efficient production and enhanced tumor delivery of engineered extracellular vesicles*, Biomaterials, 105, 195-205) describe a method for producing vesicles making it possible to increase the amount of vesicles produced. This method consists in culturing HEK293-type adherent cells in culture flasks, then in hollow fiber membranes. The central passage of the hollow fibers makes it possible to convey the culture medium to the producer cells. The producer cells are previously seeded around this passage, where they produce vesicles in an inter-fiber space. The liquid medium comprised in the inter-fiber space is collected three times per week, making it possible to produce about $3 \times 10^{12}$ vesicles in several weeks, for very large amounts of seeded cells, for example of the order of $5 \times 10^8$ cells, resulting in a yield of about 6000 extracellular vesicles per cell and a very low purity ratio (for example $1.09 \times 10^9$ particles per microgram of proteins). This production is, however, not high enough and too slow in view of the above-mentioned applications. In addition, this method is described by using producer cells corresponding to a cell line particularly resistant to culture in serum-free medium: this method may not be transposable to a production of vesicles by producer cells such as stem cells, for example human, less resistant and particularly suitable for targeted therapeutic applications.

It is also well known to a person skilled in the art that the culture of 3-dimensional (3D) suspension cells requires the use of a low-agitation method in order to not induce the death of the cells that it is sought to culture. It is notably known to a person skilled in the art that the length of Kolmogorov is a criterion that makes it possible to evaluate the turbulence created by the mixing action and to determine when the turbulence is excessive for a 3D culture.

SUMMARY

Surprisingly and unexpectedly and contrary to the commonly accepted ideas in the field of 3D cells culture, the inventors have discovered that the generation of a turbulent flow in the culture medium makes it possible to obtain a rapid production of vesicles in large quantities and to obtain their loading.

Thus, an aim of the invention is to propose a solution for rapidly producing extracellular vesicles in large quantity from producer cells, more rapidly than with the known methods, under conditions conforming to or capable of being made conforming to GMP standards. Another aim of the invention is to propose a solution for increasing the yield of the vesicles production system, i.e. the ratio between the number of vesicles produced and the number of producer cells introduced into the production system. Another aim of the invention is to provide a system suitable for producing extracellular vesicles from a wide range of suspended producer cells, regardless of the resistance of the type of cell introduced into the production system and resistant or not to serum deficiency. According to another aspect of the invention, the suspended producer cells are of human, animal, plant, bacterial or other microorganisms origin. Another aim of the invention is to propose a solution for producing and recovering extracellular vesicles continuously or discontinuously. Finally, another aim of the invention is to simplify the structure of the fluidic system for the production of vesicles and to reduce its manufacturing cost. One of the aims of the invention is also the use of the vesicles produced by the fluidic system according to the invention, and/or obtained by means of the method for ex vivo production of extracellular vesicles from suspended producer cells according to the invention. Alternatively, another aim of the invention is to propose a solution for loading the extracellular vesicles produced by the fluidic system of at least one therapeutic agent and/or imaging agent. One of the aims of the invention is also the use of the extracellular vesicles loaded with at least one therapeutic agent and/or imaging agent obtained by the method for loading at least one therapeutic and/or imaging agent into the interior or at the membrane of extracellular vesicles from producer cells according to the invention.

In particular, an object of the invention is a fluidic system for producing extracellular vesicles (EV) from suspended producer cells, comprising at least one container, a liquid medium contained by the container, suspended producer cells, a liquid medium agitator, means for controlling the speed of the agitator adapted for the growth of the suspended producer cells, characterized in that it also comprises means for controlling the speed of the agitator and an agitator whose shape and dimensions of the container are adapted to the generation of a turbulent flow of the liquid medium in the container in order to exert shear stresses on the producer cells in order to achieve the production of extracellular vesicles (EV), the length of Kolmogorov of the flow being less than or equal to 50 μm, preferably less than or equal to 40 μm; more preferably less than or equal to 35 μm. According to one embodiment, the length of Kolmogorov is from 5 to 50 μm, preferably from 5 to 41 μm, more preferably from 5 to 35 μm, even more preferably from 10 to 35 μm.

In other words, an object of the invention is a fluidic system for producing extracellular vesicles (EV) from suspended producer cells, comprising at least one container, a liquid medium contained by the container, suspended producer cells, a liquid medium agitator, means for controlling the speed of the agitator adapted for the growth of the suspended producer cells, characterized in that the means for controlling the speed of the agitator, the agitator and the shape and the dimensions of the container are suitable for generating a turbulent flow of the liquid medium in the container in order to exert shear stresses on the producer cells in order to achieve the production of extracellular vesicles (EV), the Kolmogorov length of the flow being less than or equal to 50 μm, preferably less than or equal to 40 μm; more preferably less than or equal to 35 μm. According to one embodiment, the length of Kolmogorov is from 5 to 50 μm, preferably from 5 to 41 μm, preferably from 10 to 41 μm, more preferably from 5 to 35 μm, even more preferably from 10 to 35 μm.

According to one embodiment, the producer cells used in the context of the present invention are human cells, preferably healthy human cells.

Alternatively, the producer cells used in the context of the present invention are pathological cells, for example cancer cells such as HeLa cells.

According to one embodiment, the producer cells used in the context of the present invention are animal cells, preferably murine cells, for example murine MSC cells (murine mesenchymal stem cells).

According to a preferred feature, the producer cells used in the context of the present invention are non-adherent cells.

According to another preferred feature, the producer cells used in the context of the present invention are adherent cells detached from their culture support, for example by suitable treatment, for example enzymatic, for example chemical or for example mechanical or a combination of these means.

According to one embodiment, the producer cells used in the context of the present invention are stem cells, in particular induced pluripotent stem cells, multipotent cells, for example multipotent mesenchymal cells, genetically modified cells or umbilical cord vein endothelial cells (HUVEC).

According to one embodiment, the producer cells used in the context of the present invention are stem cells, in particular induced pluripotent stem cells, multipotent cells, for example multipotent mesenchymal cells, genetically modified cells or umbilical cord vein endothelial cells (HUVEC) or primary cells in general.

According to another embodiment, the producer cells used in the context of the present invention are cell line cells, preferably of human monocyte cell line or human cell line of hematopoietic origin derived from B lymphocytes, more preferably it is THP-1 cells or Raji cells.

According to another embodiment, the producer cells used in the context of the present invention are primary cells, for example red blood cells.

According to a preferred feature, the producer cells used in the context of the present invention are cells from the subject for which the extracellular vesicles produced by said producer cells will be used, for example by administration or by ex vivo use.

According to another preferred feature, the producer cells used in the context of the present invention are cells not originating from the subject for which the extracellular vesicles produced by said producer cells will be used, for example by administration or by ex vivo use. According to a more preferred feature, the producer cells used in the context of the present invention are cells from the same species as the species of the subject for which the extracellular vesicles produced by said producer cells will be used. Alternatively, the producer cells used in the context of the present invention are cells from a species different from the species of the subject for which the extracellular vesicles produced by said producer cells will be used.

According to a preferred feature, the concentration of the producer cells in the liquid medium of the fluidic system container is between 50,000 and 500,000,000 producer cells per liter of liquid medium, preferably between 50,000,000 and 500,000,000 producer cells per liter, preferably between 50,000,000 and 300,000,000 per liter, more preferably between 200,000,000 and 300,000,000 per liter, even more preferably about 250,000,000 per liter of said liquid medium. According to another preferred feature, the concentration of the producer cells in the liquid medium of the fluidic system container is between 100,000 and 250,000,000 producer cells per liter of liquid medium.

According to a preferred feature, the concentration of the producer cells in the liquid medium of the fluidic system container is between 50,000 and 900,000,000,000,000 producer cells per liter of liquid medium, preferably between 50,000,000 and 100,000,000,000,000 producer cells per liter, preferably between 50,000,000 and 10,000,000,000,000, even more preferably between 200,000,000 and 1,000,000,000,000 per liter. According to another preferred feature, the concentration of the producer cells in the liquid medium of the container of the fluidic system is between 100,000,000 and 1,000,000,000,000 producer cells per liter of liquid medium.

In particular, an object of the invention consists of the vesicles produced by the fluidic system according to the invention.

In particular, an object of the invention is the use of the vesicles produced by the fluidic system according to the invention for acting on cells.

In particular, an object of the invention is the use of the vesicles produced by the fluidic system according to the invention for imaging and/or for therapeutic purposes.

According to one embodiment, the duration of the turbulent agitation at a length of Kolmogorov less than or equal to 50 μm, for example from 17 to 35 μm, is greater than or equal to 15 minutes, preferably from about 20 minutes to about 10 hours, more preferably from about 20 minutes to about 8 hours, even more preferentially from about 1 hour to about 6 hours, even more preferably between about 2 hours and about 3 hours, even more preferably about 2 hours or alternatively about 3 hours or alternatively about 4 hours.

According to one embodiment, the agitator of the fluidic system for producing extracellular vesicles from suspended producer cells according to the invention consists of a blade. Alternatively, said agitator consists of 2, 3, 4, 5, 6, 7, 8 or more than 8 blades.

According to a preferred feature, the at least one blade of said agitator is a vertical blade.

According to one embodiment, the agitator of the fluidic system for producing extracellular vesicles from suspended producer cells according to the invention is an agitator of the propeller type, for example marine or propeller with profiled blades, or a turbine, for example a Rushton turbine, or an agitation anchor, or a barrier agitator, or a helical ribbon propeller, or a bladed wheel, or a toothed wheel, or a magnetic agitator or a combination of these agitators.

In one embodiment, static structures may be present in the container, for example baffles, or structures forming partial barriers to liquid movement, such as those used in a static mixer.

It is understood that with such a system, it is possible to produce vesicles in large quantity, and in a system adapted or which can be adapted to GMP standards. It is also understood that such a system is simpler and less expensive to manufacture than known systems for producing extracellular vesicles.

The invention is advantageously completed by the following features, taken individually or in any of their technically possible combinations:

the agitator of the liquid medium and the dimensions of the container are adapted to control a flow of the liquid medium, the length of Kolmogorov of the flow being less than or equal to 50 μm, and preferably less than or equal to 40 μm; more preferably less than or equal to 35 μm.

the fluidic system comprises an output and a connector connected to the output, the connector being capable of comprising liquid medium and extracellular vesicles;

the agitator is preferably a rotary or orbital agitator, the shape and size of which are adapted, with the shape and dimensions of the container, to the generation of a turbulent flow of the liquid medium in the container;

the container is used or can be used in a batch mode, that is, the liquid contained in the container is extracted after the producer cells produce extracellular vesicles for a given time, the fluidic system comprises an extracellular vesicles separator, the fluidic system comprises an extracellular vesicles separator fluidly connected to the container so as to be capable of reintroducing into the container a liquid medium depleted in extracellular vesicles (EV).

the separator is positioned inside or outside the container, the liquid can be contained in the container and depleted in vesicles by means of a separator internal to the container, while the cells are held in the container or the liquid can be contained in the container and depleted in vesicles by means of a separator external to the container.

the input of the separator being fluidly connected to the container, the output of the separator being fluidly connected to the container so as to be capable of being reintroduced into the container in the form of a liquid medium depleted in vesicles.

According to one embodiment, the container of the fluidic system for producing extracellular vesicles from suspended producer cells according to the invention is a spinner flask with a capacity of 100 mL (for example the device Spinner stirring flask Bellco for cell suspensions, reference Bellco 505001), comprising a blade with a diameter of 3.8 cm and a working volume of less than 100 mL.

According to another embodiment, the container of the fluidic system for producing extracellular vesicles from suspended producer cells according to the invention is a spinner flask whose structural features (capacity, diameter of the blade and working volume) are all increased or decreased proportionally to those mentioned above for the spinner flask with a capacity of 100 mL; according to another embodiment, said structural features are all increased or decreased in a non-proportional manner with respect to those mentioned above for the spinner flask with a capacity of 100 mL, in particular during a change in scale.

According to one embodiment, the container of the fluidic system for producing extracellular vesicles from suspended producer cells according to the invention is a spinner flask with a capacity of 500 mL (for example the device Spinner stirring flask Bellco for cell suspensions, reference Bellco 505010), comprising a blade with a diameter of 7.6 cm and a working volume of 200 mL to 500 mL, or a spinner flask whose structural characteristics (capacity, diameter of the blade and working volume) are all increased or decreased proportionally to those mentioned above for the spinner flask with a capacity of 500 mL, or a stirring flange, the structural characteristics of which are all increased or decreased in a non-proportional manner with respect to those mentioned above for the spinner flask with a capacity of 500 mL, in particular during a scale change.

According to one embodiment, the container of the fluidic system for producing extracellular vesicles from suspended producer cells according to the invention is a spinner flask with a capacity of 1000 mL (for example the Spinner stirring flask Bellco for cell suspensions, reference Bellco 505010), comprising a blade with a diameter of 10.8 cm and a working volume greater than or equal to 300 mL and less than 1 L, or a spinner flask whose structural characteristics (capacity, diameter of the blade and working volume) are all increased or decreased in proportion to those mentioned above for the spinner flask with a capacity of 1000 mL.

According to another embodiment, the container of the fluidic system for producing extracellular vesicles from suspended producer cells according to the invention is a bioreactor, the working volume of which is from 400 mL to 1000 mL and the diameter of the blade of which is 6 cm.

According to another embodiment, the container of the fluidic system for producing extracellular vesicles from suspended producer cells according to the invention is a bioreactor whose working volume and diameter of the blade are increased or decreased proportionally to the respective values of 400 mL and 6 cm.

According to another embodiment, the container of the fluidic system for producing extracellular vesicles from suspended producer cells according to the invention is a bioreactor with means of agitation by blade, of which the person skilled in the art can have or design.

According to another embodiment, the container of the fluidic system for producing extracellular vesicles from suspended producer cells according to the invention is a bioreactor whose working volume and diameter of the blade are increased or decreased in a non-proportional manner with respect to the respective values mentioned above, in particular during a change in scale.

According to another embodiment, the container of the fluidic system for producing extracellular vesicles from suspended producer cells according to the invention is a bioreactor or a spinner flask whose geometric characteristics, working volume, type of mixer and characteristics, and operating mode are chosen according to practices accessible by a person skilled in the art.

Another object of the invention is a method for ex vivo production of extracellular vesicles (EV) from suspended producer cells, comprising:

a means for controlling the speed of an agitator suitable for the growth of the suspended producer cells, and the shape and dimensions of the container are adapted for generating a turbulent flow of the liquid medium in the container in order to exert shear stresses on the producer cells in order to achieve the production of extracellular vesicles (EV), the length of Kolmogorov of the flow being less than or equal to 50 μm, preferably less than or equal to 40 μm in a container, the container comprising an output, the liquid medium comprising suspended producer cells, and a collection of the liquid medium comprising extracellular vesicles (EV) at the output of the container.

The method is advantageously completed by the following features, taken individually or in any of their technically possible combinations:

the liquid medium is agitated for at least twenty minutes;

the agitator is controlled to cause a constant or intermittent flow of the liquid medium, of increasing or decreasing intensity, the length of Kolmogorov of the flow being less than or equal to 40 μm;

a separator depletes part of the liquid medium collected at the output of the container of extracellular vesicles, and the part of the liquid medium is reintroduced into the container.

The method is alternately completed by the following features, taken individually or in any of their technically possible combinations:

the method comprises a prior step of loading at least one therapeutic and/or imaging agent present in the liquid medium, the flow of the liquid medium makes it possible to simultaneously charge the at least one therapeutic and/or imaging agent inside the producer cells and produce the extracellular vesicles (EV) in a container.

The invention thus relates to a method for ex vivo production of extracellular vesicles from suspended producer cells, comprising:

(i) inserting producer cells into a container comprising a liquid medium;

(ii) actuating a control of an agitator causing a turbulent flow of the liquid medium, the length of Kolmogorov of the flow being less than or equal to 50 μm, preferably less than or equal to 40 μm, said flow allowing the extracellular vesicles to be produced in said container; and (iii) collecting the liquid medium comprising the extracellular vesicles produced in step (ii).

According to one embodiment, the container in which the producer cells are inserted in step (i) is a fluidic system for producing extracellular vesicles from suspended producer cells according to the invention as described in the present application.

In particular, an object of the invention consists of the vesicles obtained by the method for ex vivo production of extracellular vesicles from suspended producer cells according to the invention.

In particular, an object of the invention is the use of the vesicles obtained by the method for ex vivo production of extracellular vesicles from suspended producer cells according to the invention for acting on cells.

In particular, an object of the invention is the use of the vesicles obtained by the method for ex vivo production of extracellular vesicles from suspended producer cells according to the invention for imaging and/or for therapeutic purposes.

According to a similar object, the invention is a method for loading at least one therapeutic and/or imaging agent into the interior or at the membrane of extracellular vesicles (EV) from producer cells, comprising the following steps:

adding in a container a liquid medium comprising producer cells and at least one therapeutic and/or imaging agent, actuating a control of an agitator causing a turbulent flow of a liquid medium, the length of Kolmogorov of the flow being less than or equal to 50 μm, preferably less than or equal to 40 μm, said flow allowing to simultaneously charge the at least one therapeutic agent and produce the extracellular vesicles (EV) in the container, the container comprising an output, collecting the liquid medium comprising extracellular vesicles (EV) at the output of the container.

The method is alternately completed by the following features, taken individually or in any of their technically possible combinations:

the agitator is controlled to cause a flow of the liquid medium, the length of Kolmogorov of the flow being less than or equal to 40 μm;

the extracellular vesicles (EV) at the output of the container comprise a mixture of extracellular vesicles loaded with at least one therapeutic and/or imaging agent or non-charged extracellular vesicles.

According to one embodiment, the at least one medical imaging agent is chosen, for example from a fluorescence agent, a luminescence agent, a radioactive isotope, a contrast agent with magnetic, plasmonic, acoustic or radio opaque properties and mixtures thereof.

The preferred features in particular as to the type of producer cells, their concentration in the liquid medium, the Kolmogorov length ranges, the duration of the turbulent agitation at a length of Kolmogorov less than or equal to 50 μm, for example from 5 to 35 μm, and the capacity, working medium, type of agitator and diameter of the optional at least one blade of the fluidic system, which are described for the above fluidic system, are also preferred features of the methods according to the invention, namely the method for ex vivo production of extracellular vesicles from suspended producer cells and the method for loading at least one therapeutic and/or imaging agent into the interior or at the membrane of extracellular vesicles from producer cells.

In particular, an object of the invention consists of the vesicles obtained by the method of loading at least one therapeutic and/or imaging agent into the interior or at the membrane of extracellular vesicles from producer cells according to the invention.

In particular, an object of the invention is the use of the vesicles obtained by the method for loading at least one therapeutic and/or imaging agent into the interior or at the membrane of extracellular vesicles from producer cells according to the invention for acting on cells.

In particular, an object of the invention is the use of the vesicles obtained by the method of loading at least one therapeutic and/or imaging agent into the interior or at the membrane of extracellular vesicles from producer cells according to the invention for imaging and/or for therapeutic purposes.

The invention also relates to the extracellular vesicles produced by the system for producing extracellular vesicles from suspended producer cells according to the invention.

The invention also relates to the extracellular vesicles obtained by the method for producing and recovering extracellular vesicles according to the invention.

The invention also relates to the extracellular vesicles obtained by the method for loading extracellular vesicles according to the invention.

The invention also relates to the extracellular vesicles obtained by implementing the fluidic system according to the invention as described in the present application, and/or by the method for ex vivo production of extracellular vesicles (EV) from suspended producer cells according to the invention as described in the present application, and/or by the method for loading at least one therapeutic and/or imaging agent into the interior or at the membrane of extracellular vesicles (EV) from producer cells according to the invention as described in the present application.

It is well known to a person skilled in the art that the structure of the extracellular vesicles varies depending on the producer cells used and depending on the obtaining method used, in particular in terms of membrane markers and constituents present on these vesicles.

According to one embodiment, the extracellular vesicles according to the present invention have an average diameter of between 40 and 300 nm, preferably between 45 and 90 nm, more preferably between 50 and 65 nm, even more preferably about 60 nm, said mean diameter of the extracellular vesicles being measured by an interferometry method in combination or not with fluorescence, preferably said mean diameter is measured by the apparatus ExoView™ R100 marketed by the company NanoView Bioscience.

According to one embodiment, the extracellular vesicles according to the present invention have an average diameter of between 50 and 500 nm, preferably between 100 and 110 nm, more preferably between 105 and 109 nm, even more preferably about 106 nm or about 108 nm, said mean diameter of the extracellular vesicles being measured by a method for individual tracking of particles (or NTA for Nanoparticle Tracking Analysis), for example with the apparatus NanoSight NS300 sold by the company Malvern Panalytical.

Advantageously, said extracellular vesicles have membrane markers CD81, CD63, and/or CD9 as described in FIG. 11. More advantageously, said extracellular vesicles express the markers CD81 and/or CD63. The extracellular vesicles produced from the fluidic system according to the invention and/or according to the method according to the invention can be cooled to a desired temperature, for example about 4 degrees centigrade, or they may be frozen if desired for transport.

The invention also relates to the use of the extracellular vesicles produced by the fluidic system according to the invention as described in the present application, and/or obtained by means of the method for ex vivo production of extracellular vesicles (EV) from suspended producer cells according to the invention as described in the present application, and/or obtained by means of the method for loading at least one therapeutic and/or imaging agent into the interior or at the membrane of extracellular vesicles (EV) from producer cells according to the invention as described in the present application, as a vector for the administration of at least one medical imaging agent, for example for performing medical imaging. According to one embodiment, the at least one medical imaging agent is chosen, for example, from a fluorescence agent, a luminescence agent, a radioactive isotope, a contrast agent with magnetic, plasmonic, acoustic or radio opaque properties and mixtures thereof.

The present invention also relates to the extracellular vesicles produced by the fluidic system according to the invention as described in the present application, and/or obtained by means of the method for ex vivo production of extracellular vesicles (EV) from suspended producer cells according to the invention as described in the present application, and/or obtained by means of the method for loading at least one therapeutic and/or imaging agent into the interior or at the membrane of extracellular vesicles (EV) from producer cells according to the invention as described in the present application, for their therapeutic use.

The present invention also relates to the extracellular vesicles produced by the fluidic system according to the invention as described in the present application, and/or obtained by means of the method for ex vivo production of extracellular vesicles (EV) from suspended producer cells according to the invention as described in the present application, and/or obtained by means of the method for loading at least one therapeutic and/or imaging agent into the interior or at the membrane of extracellular vesicles (EV) from producer cells according to the invention as described in the present application, for their use in immunotherapy, in regenerative medicine, as an alternative or in addition to the cell therapy, as a vector for delivering at least one therapeutic and/or imaging agent and/or in the treatment of tumors, infectious diseases, inflammatory diseases, immunological diseases, metabolic diseases, cancer diseases, genetic diseases, degenerative diseases or diseases secondary to surgeries or trauma.

The present invention also relates to a method of treatment in immunotherapy, in regenerative medicine, as an alternative or in addition to cell therapy, as vectors of at least one therapeutic and/or imaging agent, and/or for the treatment of tumors, infectious diseases, inflammatory diseases, immunological diseases, metabolic diseases, cancer diseases, genetic diseases, degenerative diseases or diseases secondary to surgeries or trauma, involving the administration to a subject in need thereof of extracellular vesicles produced by the fluidic system according to the invention as described in the present application, and/or obtained by the method for ex vivo production of extracellular vesicles (EV) from suspended producer cells according to the invention as described in the present application, and/or obtained by means of the method for loading at least one therapeutic and/or imaging agent into the interior or at the membrane of extracellular vesicles (EV) from producer cells according to the invention as described in the present application.

The present invention also relates to the use of the extracellular vesicles produced by the fluidic system according to the invention as described in the present application, and/or obtained by means of the method for ex vivo production of extracellular vesicles (EV) from suspended producer cells according to the invention as described in the present application, and/or obtained by means of the method for loading at least one therapeutic and/or imaging agent into the interior or at the membrane of extracellular vesicles (EV) from producer cells according to the invention as described in the present application, for the manufacture of a medicament used in immunotherapy, in regenerative medicine, as an alternative or in addition to the cell therapy, as a vector of at least one therapeutic and/or imaging agent, and/or used in the treatment of tumors, infectious diseases, inflammatory diseases, immunological diseases, metabolic diseases, cancer diseases, genetic diseases, degenerative diseases or diseases secondary to surgeries or traumas.

According to one embodiment, the therapeutic use of the extracellular vesicles, the extracellular vesicles for their therapeutic use, the methods of treatment or the use of the extracellular vesicles for their use for the manufacture of a medicament, as described above, involves the administration and/or the ex vivo use of said extracellular vesicles. The administration may, for example, be parenteral or enteral, such as injectable administration (in particular intravenous, intramuscular, subcutaneous, intraspinal, etc.), oral, buccal, cutaneous, local, vaginal, rectal, ocular, auricular, etc.

According to a preferred feature, the invention relates to the extracellular vesicles according to the invention, as described in the present application, obtained from THP-1 producer cells or from lymphocytes, for their use, for example in immunotherapy and/or cancerology.

According to another preferred feature, the invention relates to the extracellular vesicles according to the invention, as described in the present application, obtained from producer cells which are mesenchymal stem cells (MSC), for their use in regenerative medicine or in the treatment of tumors, infectious diseases, inflammatory diseases, immunological diseases, metabolic diseases, cancer diseases, genetic diseases, degenerative diseases or diseases secondary to surgeries or traumas.

According to another preferred feature, the invention relates to the extracellular vesicles according to the invention, as described in the present application, obtained from any type of cells or from red blood cells, and loaded with at least one therapeutic agent, for their use in delivering the at least one therapeutic agent into the body of a subject.

According to another preferred feature, the invention relates to the use of the extracellular vesicles according to the invention, as described in the present application, obtained from any type of cells or from red blood cells, and loaded with at least one imaging agent, for performing a medical imaging examination.

According to another preferred feature, the invention relates to the use of the extracellular vesicles according to the invention, as described in the present application, obtained from any type of cell or from red blood cells, and loaded with at least one therapeutic agent and at least one imaging agent, for performing the tracking of the distribution of said extracellular vesicles in the body of a subject by medical imaging and delivering the at least one therapeutic agent into the body of said subject.

The term "extracellular vesicle" generally denotes a vesicle which is endogenously released by a producer cell, the diameter of which is between 30 nm and 5000 nm. An extracellular vesicle particularly corresponds to an exosome and/or a microvesicle and/or a cellular apoptotic body.

The term "suspended producer cell" generally refers to a cell which is not adherent to a medium and can divide and multiply. According to another aspect of the invention, the term "suspended producer cells" denotes human cells, cells of animal or plant origin, bacteria or other microorganisms capable of secreting extracellular vesicles. According to another aspect of the invention, the term "suspended producer cells" denotes adherent cells detached from their culture support and suspended. A mild mixture created by the agitator allows the suspended producer cells as defined to remain suspended in the liquid culture medium. According to another aspect of the invention, the term "suspended producer cells" denotes cell aggregates. The term "cellular aggregates" refers to an assembly of a plurality of suspended producer cells that adhere to each other. A mild mixture created by the agitator allows the suspended producer cells as defined to remain suspended in the liquid culture medium.

The term "therapeutic agent" or "imaging agent" generally refers to any agent, molecule or particle, compound of interest capable of being charged, inserted into the extracellular vesicles. These agents may be therapeutic molecules or particles for treating infectious, inflammatory, metabolic, degenerative, traumatic, post-surgical, genetic, malignant (tumors) or orphan diseases, or diseases of the vascular, lymphatic, locomotor, digestive, nerve, reproductive or excretory systems, and/or agents (molecules or particles) of nuclear imaging, magnetic imaging, optical imaging, acoustic imaging, etc. Thus, the at least one medical imaging agent according to the present invention can advantageously be chosen from a fluorescence agent, a luminescence agent, a radioactive isotope, a contrast agent with magnetic, plasmonic, acoustic or radio opaque properties and mixtures thereof.

The term "agitator" should be understood in an extremely general direction, which is that of a means or a combination of means allowing by action on the liquid to generate at least one flow, to promote mixing of the liquid or to generate turbulence in this liquid.

The term "approximately" or "about", placed in front of a number, means more or less than 10% of the nominal value of this number.

The term "cell" refers to the smallest fundamental structural and functional unit of living organisms, consisting of a protoplasm or cytoplasm, separated from the external medium by a membrane. In the context of the present invention, the term "cell" also encompasses red blood cells and platelets.

The term "healthy cells" denotes cells derived from healthy tissues, as opposed to cells derived from pathological tissues or organs, i.e. the functions of which are altered.

The term "between X and Y" relates to the range of values between X and Y, the terminals X and Y being included in said range.

The term "immunotherapy" refers to the treatment of a disease by an intervention on the immune system.

The term "regenerative medicine" refers to all biomedical methods used for the replacement or regeneration of human tissues or organs for therapeutic purposes.

The term "subject" denotes an animal, including a human, male or female, regardless of the age. In the sense of the present invention, a subject can be a patient, namely a person receiving medical care, undergoing or having undergone medical treatment, or monitored in the context of the development of a disease.

The term "cellular therapy" refers to the use in humans of living somatic cells, manipulated or modified in their biological characteristics, in order to prevent, treat, or alleviate some pathologies.

BRIEF DESCRIPTION OF THE FIGURES

Other features and advantages will become apparent from the following description, which is purely illustrative and non-limiting, and must be read in conjunction with the attached figures, among which.

DETAILED DESCRIPTION

Theoretical Elements

The length of Kolmogorov (or dimension of Kolmogorov or length of eddy) is the length from which the viscosity of a fluid makes it possible to dissipate the kinetic energy of a flow of this fluid. In practice, the length of Kolmogorov corresponds to the size of the smallest vortices in a turbulent flow. This length $L_K$ is calculated in the publication of Kolmogorov (Kolmogorov, A. N., 1941, January, *The local structure of turbulence in incompressible viscous fluid for very large Reynolds numbers*, In Dokl. Akad. Nauk, SSSR, Vol. 30, No. 4, pp. 301-305) and described by the following formula (I):

[Math 1]
$$L_k = v^{3/4} \cdot \varepsilon^{-1/4} \quad (I)$$

in which v is the kinematic viscosity of the flowing liquid medium and ε is the average rate of energy dissipation in the fluid per mass unit (or energy injection rate in the fluid).

Zhou et al. (Zhou, G., Kresta, S. M., 1996, *Impact of tank geometry on the maximum turbulence energy dissipation rate for impellers*, AIChE journal, 42(9), 2476-2490) describe the relationship between the mean c and the geometry of a container in which a liquid medium is agitated by a paddle wheel type agitator. This relationship is given by the following formula (II):

[Math 2]
$$\varepsilon = \frac{N_p \cdot D^5 \cdot N^3}{V} \quad (II)$$

in which $N_p$ is the dimensionless number of power (or number of Newton) of the agitator in the liquid medium, D is the diameter of the agitator (meter), N is the speed of rotation (in number of rotation per second) and V is the volume of liquid medium (per cubic meter). This relationship is used for the calculation of the mean ε corresponding to the geometry of a container and an agitator used for the implementation of the invention. The number of power $N_p$ is given in a known way by the formula (III):

[Math 3]

$$N_p = \frac{P}{N^3 D^5 \rho} \tag{III}$$

in which P is the power supplied by the agitator, and p is the density of the liquid medium. Formula (III) can be adjusted as described in Nienow et al. (Nienow, A. W., & Miles, D., 1971, *Impeller power numbers in closed vessels*, Industrial & Engineering Chemistry Process Design and Development, 10(1), 41-43) or Zhou et al. (Zhou, G., Kresta, S. M., 1996, *Impact of tank geometry on the maximum turbulence energy dissipation rate for impellers*, AIChE journal, 42(9), 2476-2490) as a function of the Reynolds number of the flow of the liquid medium. It is also possible to calculate the Reynolds number of the system by the following formula (IV):

[Math 4]

$$Re = \frac{N \cdot D^2}{v} \tag{IV}$$

Alternatively, the person skilled in the art can calculate the length of Kolmogorov per unit of volume with his general knowledge and with alternative calculation modes. In any case, the calculation presented above is only one way among many others known to the person skilled in the art to calculate the length of Kolmogorov.

General Architecture of the Fluidic System

Figure 1:
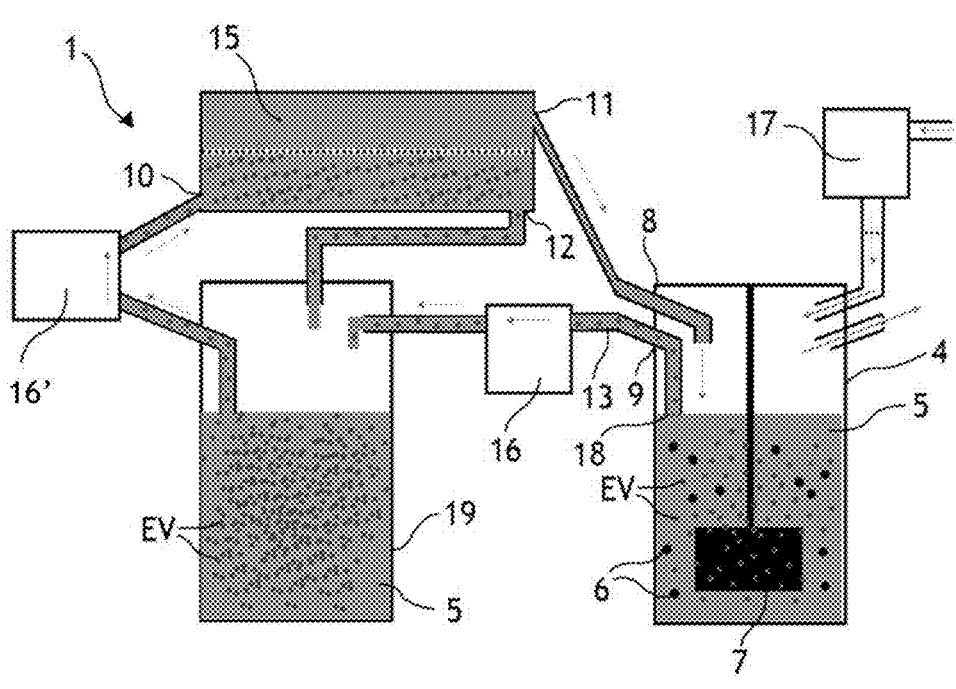
FIG. 1 schematically illustrates a fluidic system for the production of extracellular vesicles.

FIG. 1 schematically illustrates a fluidic system (1) for the production of extracellular vesicles (EV). The fluidic system (1) for producing extracellular vesicles (EV) is intended for the large quantity production of extracellular vesicles (EV) in a container (4). However, the invention is not limited to this embodiment and may comprise a series of containers (4) fluidly connected in parallel or in series.

The container (4) contains a liquid medium (5). The container (4) may in particular be a tank, a flask, for example made of glass or plastic, or any other container suitable for containing a liquid medium (5). The container may be flexible, or contain flexible portions. The volume of the container (4) is one of the factors making it possible to produce extracellular vesicles (EV) in large quantity: this volume may be between 50 mL and 500 L, preferably between 100 mL and 100 L, and preferably between 300 mL and 40 L. The volume of the container (4) illustrated schematically in FIG. 1 is 1 L. The container (4) typically comprises one or more gas inputs and one or more gas ouputs, through which can flow an atmosphere comprising concentrations of air, $O_2$, $N_2$ and $CO_2$ suitable for cell culture, for example comprising 5% $CO_2$. This atmosphere may be from a suitable gas injector/mixer or a $CO_2$ controlled atmosphere oven. A second pump (17) makes it possible to control this gas flow in the container (4). The container (4) also comprises an output (9) capable of comprising liquid medium (5) and extracellular vesicles (EV). This output can be supplemented with a means for separating and/or filtering the cells in suspension making it possible not to recover suspended cells outside the container (4). This output (9) makes it possible to extract the produced extracellular vesicles (EV) out of the container (4). The container (4) may also comprise at least one input (8) adapted to introduce the liquid medium (5) into the container (4).

The liquid medium (5) may be generally a saline solution, for example isotonic. Preferably, the liquid medium (5) is a liquid culture medium with the addition of compounds allowing the culture of the cells of interest, or a medium supplemented with serum or platelet lysate previously purified from the extracellular vesicles or a serum-free medium, making it possible not to contaminate the extracellular vesicles (EV) produced by the fluidic system (1) with proteins or other vesicles from a serum or platelet lysate. A serum-free DMEM type liquid medium (5) can be used. The maximum volume of liquid medium (5) is determined in part by the container (4). This maximum volume may also be between 50 mL and 500 L, preferably between 100 mL and 100 L, and more preferably between 300 mL and 40 L. The minimum volume of liquid medium (5) contained by the container (4) is partly determined by the choice of the agitator (7) making it possible to agitate the liquid medium (5).

The fluidic system (1) also comprises suspended producer cells (6), the term suspended producer cells term including both the suspended cells (non-adherent cells) and the cells that have been put in suspension (adherent cells). The extracellular vesicles (EV) are produced by the fluidic system (1) from these suspended producer cells (6). The suspended producer cells (6) can be cultured, before the production of extracellular vesicles (EV) by the fluidic system (1) in a suitable cell culture medium. Thus, no cell transfer is required between the culture of the suspended producer cells (6) and the production of the extracellular vesicles (EV), thereby avoiding contamination and simplifying the process as a whole. The majority of the suspended producer cells (6) are suspended homogeneously in the medium, even if a minority proportion of suspended producer cells (6) can be sedimented at the bottom of the container (4) or adhered to the wall of the container (4), for example by stirring the liquid medium (5). Preferably, the fluidic system (1) is adapted so as to generate a gentle agitation making it possible to homogenize the producer cells (6) in the liquid medium (5) within the container (4), preferably before the production of the extracellular vesicles. In general, any type of producer cells (6) can be used, preferably non-adherent suspended producer cells (6).

The container (4) also comprises an agitator (7) for agitating the liquid medium (5). The agitator (7) may be an impeller, the blades of which are at least partially immersed in the liquid medium (5), and moved by a transmission of magnetic or mechanical forces. The agitator (7) may also be a liquid medium infusion system (5) at a flow rate sufficient to agitate the liquid medium (5) contained by the container, or a rotary wall system (e.g. arranged on rollers). The agitator (7) may alternatively be of a bottle roller, an orbital agitator for Erlenmeyer flasks, with or without shaken flask, a wave agitator, a biorecipient with pneumatic agitation (air-lift) or a rotary agitator with blades such as a marine propeller, a Rushton turbine, an anchor agitator, a barrier agitator, a helical ribbon agitator. A preferred rotary agitator is a vertical blade turbine. Finally, static structures may be present in the container, for example baffles, or structures forming partial barriers to liquid movement, such as those used in a static mixer, may naturally also be used. The agitator (7) and the dimensions of the container (4) are adapted to control a turbulent flow of the liquid medium (5) in the container (4). The person skilled in the art of his general knowledge knows how to calculate the length of Kolmogorov suitable for each type of agitator (7) as a function of the dimensions of the container (4), the geometry of the agitator (7) and the intensity of the agitation. The term "turbulent flow" means a flow whose Reynolds number is greater than 2000. The Reynolds number can for example be calculated by formula (IV). Preferably, the Reynolds number Re of the liquid medium (5) flow is greater than 7,000, preferably than 10,000 and preferentially than 12,000.

Other agitators (7) for controlling a turbulent flow according to the present invention are well-known agitators of a person skilled in the art and capable of being implanted in the system according to the present invention.

The agitator (7) used in the exemplary embodiments of the invention comprises a paddle wheel or a blade arranged in a container (4) and moved by a system for transmitting magnetic or mechanical forces. The speed of the paddle wheel or blade in the liquid medium (5) results in a flow of the liquid medium (5). The agitator is adapted to control a flow, which, in view of the dimensions of the container (4), is turbulent. In the case of the agitator (7) illustrated in FIG. 1, several parameters make it possible to calculate a value representative of the turbulence of the liquid medium (5), in particular the kinematic viscosity v of the liquid medium (5), the dimensions of the container (4) and in particular the volume V of liquid medium (5) contained in the container (4), the number of power $N_p$ corresponding to the submerged part of the paddle wheel or of the blade, the diameter D of the agitator and in particular of the wheel or of the blade, the speed N of rotation of the wheel or of the blade. The user can thus calculate, as a function of these parameters, values representative of the turbulence of the flow, and in particular the length of Kolmogorov $L_K$, as given by equations (I), (II) and (III). In particular, the agitator (7) is adapted to control a flow in which the length $L_K$ is less than or equal to 50 μm and preferably less than or equal to 40 μm.

In an exemplary embodiment of the fluidic system (1), the speed of rotation of the agitator (7) is capable of being controlled at 500 rpm (rotations per minute), for example, the diameter of a paddle wheel or blade is 10.8 cm and the volume of liquid medium contained by the container (4) is 400 mL. The measured number of power NP of the paddle wheel or blade in the liquid medium (5), by formula (III), is substantially equal to 3.2. The energy dissipated per unit of mass ε, calculated by formula (II), is equal to $6.80 \times 10^{-1}$ J·kg$^{-1}$. The length of Kolmogorov $L_K$ calculated by formula (I) is thus equal to 11.0 μm.

Therapeutic or Imaging Agent Loading Aspect

The fluidic system (1) for the production of extracellular vesicles (EV) is intended for the large quantity production of extracellular vesicles (EV) in a container (4). However, the invention is not limited to this embodiment and also allows the loading of therapeutic and/or imaging agents in large quantities into the extracellular vesicles (EV) produced according to the invention. Thus, the suspended cells (6) and the at least one therapeutic and/or imaging agent are simultaneously suspended in the liquid medium (5) and mixed in the container (4). Alternatively, the suspended cells (6) can be added in the liquid medium (5) before or after the addition of the therapeutic agents and/or imaging agents in said liquid medium (5). In general, any type of therapeutic or imaging agent can be used, preferably therapeutic agents molecules or particles for treating infectious, inflammatory, metabolic, degenerative, traumatic, post-surgical, genetic, malignant (tumors), orphan, vascular, lymphatic, locomotor, digestive, nervous, reproductive, excretory diseases, and/or agents (molecules or particles) for nuclear, magnetic, optical acoustic imaging. The container (4) also comprises an agitator (7) as described above and for agitating the liquid medium (5) comprising the suspended producer cells (6) and the at least one therapeutic or imaging agent. Preferably, the fluidic system (1) is adapted to generate a gentle agitation for homogenizing the producer cells (6) in the liquid medium (5) within the container (4) to effectively charge the agents of interest in the producer cells (6) and therefore in the extracellular vesicles.

According to another object, the invention is a method for ex vivo production of extracellular vesicles from producer cells, comprising:

a control of an agitator (7) causing a turbulent flow of a liquid medium (5), the length of Kolmogorov of the flow being less than or equal to 50 μm, preferably less than or equal to 40 μm in a container (4), the container comprising an output (9), the liquid medium (5) comprising suspended producer cells (6) and the at least one therapeutic and/or imaging agent, and a collection of the liquid medium (5) comprising extracellular vesicles (EV) at the output (9) of the container (4).

Preferably, the method according to the invention comprises a step of loading at least one therapeutic and/or imaging agent. More preferably, the step of loading said at least one therapeutic and/or imaging agent is simultaneous to the step of producing extracellular vesicles. Of course, this step may also be prior to the step of producing extracellular vesicles. Alternatively, the loading step may be subsequent to the step of producing extracellular vesicles. This embodiment may be of interest in the case where it is desired to obtain a first production of unloaded vesicles followed by a second production of extracellular vesicles loaded with said at least one therapeutic and/or imaging agent, and this in the context of placing a fluidic system with a collection of the liquid medium (5) continuously. Surprisingly, the flow that allows the suspended producer cells (6) to produce extracellular vesicles also allows and simultaneously to load the at least one therapeutic and/or imaging agent in the suspended producer cells (6) and therefore produce said extracellular vesicles (EV) in a container (4) loaded with the at least one therapeutic and/or imaging agent.

In a preferred manner, the invention is a method for loading at least one therapeutic and/or imaging agent into the interior or at the membrane of the extracellular vesicles (EV) from producer cells (6), comprising the following steps:

adding in a container (4) a liquid medium (5) comprising producer cells (6) and at least one therapeutic and/or imaging agent, actuating a control of an agitator (7) resulting in a turbulent flow of a liquid medium (5), the length of Kolmogorov of the flow being less than or equal to 50 μm, preferably less than or equal to 40 μm, said flow allowing to simultaneously load the at least one therapeutic agent and produce the extracellular vesicles (EV) in a container (4), the container comprising an output (9), collecting the liquid medium (5) comprising extracellular vesicles (EV) at the output (9) of the container (4).

Preferentially the extracellular vesicles (EV) at the output (9) of the container (4) comprise a mixture of extracellular vesicles loaded with at least one therapeutic and/or imaging agent and extracellular vesicles not loaded with at least one therapeutic and/or imaging agent.

Preparation of the Culture Medium, Therapeutic Agents and/or Imaging Agents and Producer Cells The container (4) can be disposable or sterilized before any introduction of liquid medium (5), producer cells (6) and of the at least one therapeutic agent or imaging agent. The at least one therapeutic agent and/or imaging agent is incubated in the culture medium of the producer cells (6), comprising serum, in the container (4).

The producer cells (6), before being introduced into the fluidic system 1, are put in suspension by any means or a combination of means known to the skilled in the art, for example by means of a medium comprising trypsin or any other enzyme allowing the suspension of adherent cells known to a person skilled in the art. They can then be centrifuged at 300 G for five minutes to be concentrated in the base of a tube, so as to replace the medium comprising trypsin by a DMEM medium. The producer cells (6) then are introduced into the container (4), comprising culture medium and according to an alternative embodiment the at least one therapeutic agent and/or imaging agent. The producer cells (6) and the therapeutic agents and/or imaging agents are then agitated so as to contact the therapeutic agents and/or imaging agents and the producer cells (6), and promote the loading of the therapeutic agents and/or imaging agents into the producer cells (6). The agitation can resume periodically so as to promote the homogeneity of the producer cells (6) and the therapeutic agents and/or imaging agents in the liquid medium (5). For example, the homogenization of the elements present in the culture medium (5) is carried out with low agitation of the culture medium (for example the rotation of a paddle wheel at a speed of 20 rpm), as well as a regular replacement of the culture medium (for example a replacement of 5% to 40% of the culture medium each day, for example a replacement of 5%, 10%, 15%, 20%, 25%, 30%, 35% or 40% of the culture medium each day).

Example of Production of Extracellular Vesicles (EVs) without Loading a Therapeutic Agent and/or Imaging Agent The extracellular vesicles (EV) are produced in a container (4) containing a liquid medium (5), for example without serum, and suspended producer cells (6). The medium used before the production for the culture of producer cells (6) comprising serum, three to four times the container (4) is washed with liquid medium (5) DMEM without serum, each washing corresponding for example to a volume of approximately 400 mL. The agitation of the liquid medium (5) is then controlled by the agitator (7) so as to cause a turbulent flow in the container (4). The agitation is preferably adjusted so as to control a flow of the liquid medium (5) in which the length of Kolmogorov $L_K$ is less than or equal to 50 µm and preferably less than or equal to 40 µm. The agitation of the liquid medium (5) is controlled at least for twenty minutes, preferably for more than one hour, and preferably for more than two hours, for example about three hours. The production of extracellular vesicles (EV) can be measured during production. For this purpose, the agitation can be continuous, intermittent, increasing or decreasing. The producer cells (6) are allowed to settle at the bottom of the container (4), then a liquid medium sample (5) comprising EV extracellular vesicles is taken. Centrifugation of the sample is carried out at 2000 G for 10 minutes, so as to remove cell debris. The supernatant is analyzed by a method for individual tracking the particles (or NTA: Nanoparticle Tracking Analysis) so as to count the number of extracellular vesicles (EV) and to deduce therefrom the concentration of extracellular vesicles (EV) of the samples.

It can be verified that the concentration of extracellular vesicles (EV) at the beginning of the agitation is close to zero or negligible.

The extracellular vesicles (EV) produced can also be observed and/or counted by transmission electron cryo-microscopy. To this end, a drop of 2.7 µL of solution comprising extracellular vesicles (EV) is deposited on a grid suitable for cryo-microscopy, then immersed in ethane liquid, resulting in near-instantaneous freezing of said drop, avoiding the formation of ice crystals. The grid supporting the extracellular vesicles (EV) is introduced into the microscope and the extracellular vesicles (EV) are observed at a temperature of the order of −170° C.

Extracellular Vesicles Separation

The extracellular vesicles (EV) produced in the container (4) are capable of being extracted from the container (4) by the output (9) of the container (4), suspended in the liquid medium (5). A filter (18) can be arranged at the output (9) so as to filter the suspended producer cells (6) and cell debris upon extraction of extracellular vesicles (EV) from the container (4). A connector (13) is fluidically connected to the output (9), allowing the transport of the liquid medium (5) comprising the produced extracellular vesicles (EV).

The fluidic system (1) may comprise a separator (15) of extracellular vesicles (EV). The separator (15) comprises an input of the separator (10), in which the liquid medium (5) comprising extracellular vesicles (EV) from the container (4) can be fed directly or indirectly. The separator (15) may also comprise a first output (11) of the separator, through which the liquid medium (5) is able to exit the separator (15) with a smaller concentration of extracellular vesicles (EV) than at the input (10) of the separator (15), or even substantially zero. The separator (15) may also comprise a second output (12) of the separator (15), through which the liquid medium (5) is capable of exiting the separator (15) with a higher concentration of extracellular vesicles (EV) than at the input (10) of the separator (15).

In general, the separator (15) of extracellular vesicles (EV) can be fluidically connected to the container (4) so as to be capable of reintroducing a liquid medium (5) depleted in vesicles (EV) into the container (4), for example by the input (8) of the container (4). Thus, the production and/or extraction of extracellular vesicles (EV) can be carried out continuously, with a substantially constant volume of liquid medium (5) in the container (4). According to an alternative embodiment, the fluidic system does not comprise a separator (15) of extracellular vesicles (EV) or the fluidic system comprises a separator (15) of extracellular vesicles (EV) that can be fluidly connected or not, for example via a means for closing said separator (15), to the container (4). Thus, the production and/or extraction of extracellular vesicles (EV) can be carried out discontinuously or continuously according to the opening or closing of the closing means arranged upstream of the separator (15).

In the case of batch operation, the container containing the producer cells is agitated and the production duration is preferably chosen for a time (Tv) greater than 20 minutes.

The liquid can then be extracted from the container, and can be subjected to one or more subsequent purification steps, in particular for separating the vesicles from the producer cells. This separation can be achieved by means of techniques known to those skilled in the art, for example and taken in a non-limiting manner, by acoustic techniques, filtration methods such as tangential filtration separation, the use of rotary filters or any combinations of separation means.

In the case of continuous operation and according to a preferred embodiment, the separation system is internal to the container, the vesicles are gradually separated in a sub-compartment of the container. Various technical means are known to those skilled in the art in order to achieve this type of separation, for example and in a non-limitative way, the use of rotary filters, or else acoustic means, or any combinations of separation means. According to another embodiment, the system for separating cells and vesicles can involve a fluidic circuit designed to circulate the medium with the producer cells and the vesicles between the container on the one hand and a separation system outside the container on the other hand. This separation system outside the container may involve techniques known to those skilled in the art, for example, and in a non-limiting manner, of tangential filtration, or of acoustic separation, or any combinations of known separation means. At the output of the separation system, the vesicles-depleted liquid is reinjected into the container, so that the production of vesicles by the producer cells can continue in the container.

In the exemplary embodiment of a fluidic system (1) illustrated in FIG. 1, the liquid medium (5) can be extracted from the container (4) by a first pump (16), via a connector (13), so as to transport the liquid medium (5) into a collector (19). Another first pump (16') makes it possible to convey the liquid medium (5) contained in the collector (19) to the input (10) of the separator (15), via another connector. The first output (11) of the separator (15) is connected to the container (4) via a connector, so as to reintroduce liquid medium (5) depleted in extracellular vesicles (EV) into the container (4). The second output (12) of the separator (15) is connected to the collector (19) via a connector, so as to enrich the liquid medium (5) contained in the collector (19) with extracellular vesicles (EV). Alternatively, the input (10) of the separator (15) can be directly connected to the output (9) of the container (4) (or via a first pump (16)). The first output (11) of the separator (15) is connected to the container (4) and the second output (12) of the separator (15) is connected to the collector (19). Several separators may also be arranged in series to vary the degree of separation of extracellular vesicles (EV) in the liquid medium (5), and/or in parallel to adapt the flow of liquid medium (5) in each separator (15) to the flow rate of a first pump (16).

Influence of Agitation on the Production of Extracellular Vesicles (EV)

In the following figures, different types of producer cells are used. Before their use for the production of extracellular vesicles, these producer cells are cultured, except for red blood cells whose preparation before use for the production of extracellular vesicles consists in obtaining a suspension of red blood cells washed at the desired concentration in DMEM without phenol red.

THP-1 cells, derived from a human monocyte line, are cultured in the culture medium RPMI (Roswell Park Memorial Institute medium) at a concentration of $2 \times 10^5$ to $1 \times 10^6$ cells per milliliter of culture medium, at 37° C. and under an atmosphere comprising 5% $CO_2$. The culture medium RPMI contains 10% by volume of fetal bovine serum and 1% by volume of penicillin/streptomycin, the volumes being expressed relative to the total volume of the culture medium RPMI. They are all subcultured every 3 to 5 days by diluting them by a factor of 5 in fresh medium.

Raji cells, a human cell line of hematopoietic origin derived from B lymphocytes, are cultured in RPMI culture medium containing 10% by volume of fetal bovine serum and 1% by volume of penicillin/streptomycin, the volumes being expressed relative to the total volume of the RPMI culture medium. They are subcultured every 3 to 4 days by diluting them by a factor of 10 to 20 in fresh medium.

The C3H/10T1/2 cells are multipotent mesenchymal cells derived from the embryonic cells of CH3 mice, which are adherent. They are cultured in DMEM with 10% by volume of fetal bovine serum and 1% by volume of penicillin/streptomycin, the volumes being expressed relative to the total volume of the DMEM culture medium. They are subcultured every 3 to 5 days by diluting them by a factor of between 2 and 10.

The HeLa cells are a cell line derived from cervical cancer. They are cultured in DMEM with 10% by volume of fetal bovine serum and 1% by volume of penicillin/streptomycin, the volumes being expressed relative to the total volume of the DMEM culture medium. Initially adherent, these HeLa cells are detached with trypsin and then suspended in a 50 RPM stirred bioreactor, and cultured at a concentration of between $10^5$/mL and $10^6$/mL.

Before using the producer cells for the production of extracellular vesicles, the cells which have been cultured are washed and then re-suspended in white DMEM, with 1% by volume of penicillin/streptomycin relative to the volume of the DMEM medium, in the container in which the production of extracellular vesicles will take place (flask, spinner flask or bioreactor, preferably conforming to the G.M.P standards).

Figure 2:
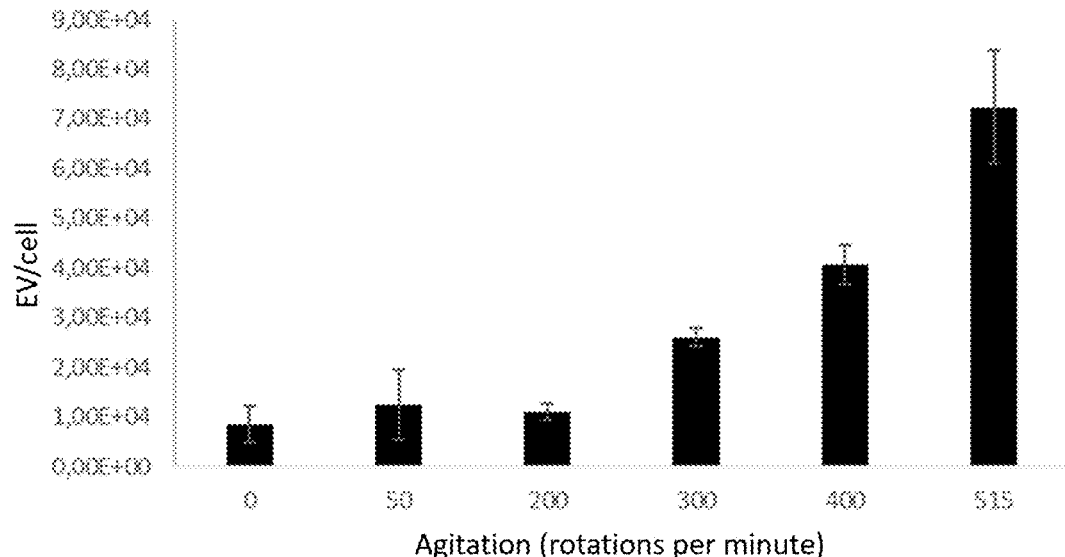
FIG. 2 illustrates the number of extracellular vesicles produced by THP1 cells in a fluidic system after 20 minutes of agitation for different intensities of agitations.

FIG. 2 illustrates the number of extracellular vesicles produced by THP-1 cells in a fluidic system (1) for different agitations controlled by the agitator (7). The ordinate corresponds to the numbers of extracellular vesicles (EV) produced by cell in the container (4). Each column corresponds to a production of extracellular vesicles (EV) for different speeds of rotation of the agitator (7) in the container (4). The extracellular vesicles (EV) are produced from producer cells (6) of THP1 type in the container (4) using a concentration of 100,000,000 cells in suspension (6) in 400 mL of liquid medium (5) in a spinner flask of 1000 mL. Significantly high production of extracellular vesicles (EV) is observable by controlling a flow of liquid medium (5) in which production corresponds to column 300 RPM i.e. a length $L_K$ equal to or less than 17 μm relative to the production of extracellular vesicles (EV) under lower agitation conditions in which the agitation speed is 200 RPM i.e. a length $L_K$ equal to 23 μm. Moreover, under even higher agitation conditions, namely 400 RPM and 515 RPM, corresponding to the obtaining of lengths $L_K$ equal respectively to 13.8 μm and 11.4 μm, the production of extracellular vesicles per producer cell further increases, inversely proportional to the length $L_K$. This illustrates that the greater the agitation, the more the producer cells produce extracellular vesicles.

Figure 3:
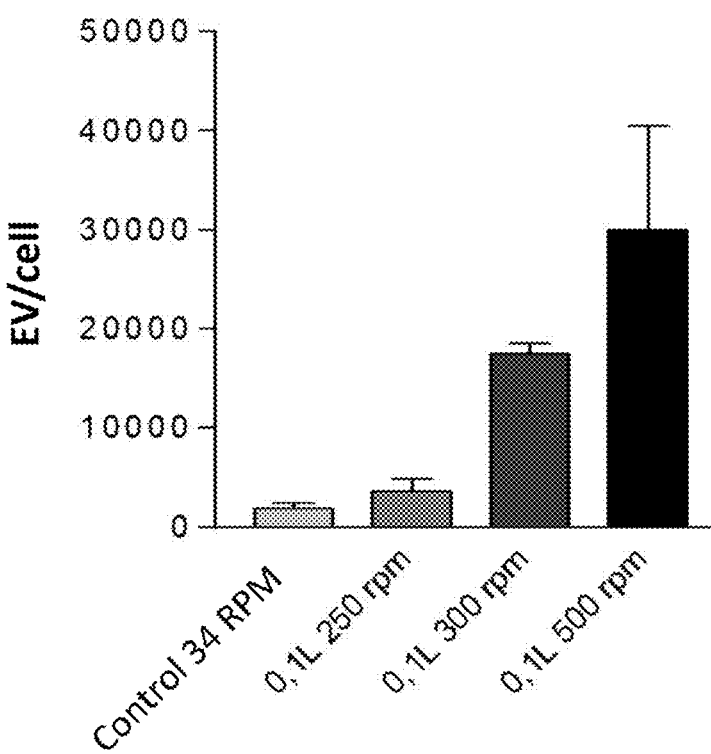
FIG. 3 illustrates the number of extracellular vesicles produced by THP1 cells after 3 hours of stirring for different intensities of agitations.

FIG. 3 illustrates the number of extracellular vesicles produced by producer cells (6) of THP-1 type for different agitations controlled by the agitator (7) in a fluidic system (1) whose container (4) and the quantity of liquid medium (5) are different from those used in the context of the experiment of FIG. 2, and over a longer agitation duration of 3 hours instead of 20 minutes. In a 0.1 L spinner flask comprising 50 mL of liquid medium (5), 3553 extracellular vesicles are produced by a producer cell in three hours under an agitation of 250 RPM performed by a blade of 3.8 cm in diameter, the length of Kolmogorov $L_K$ being 41 μm. In a 0.1 L spinner flask comprising 50 mL of liquid medium (5), approximately 17 400 extracellular vesicles are produced by producer cell in three hours under an agitation of 300 RPM performed by a blade of 3.8 cm in diameter, the length of Kolmogorov $L_K$ being equal to 35 μm. In a 0.1 L spinner flask comprising 50 mL of liquid medium (5), between 30,000 and 40,000 extracellular vesicles are produced by a producer cell in three hours under an agitation of 500 RPM performed by a blade of 3.8 cm in diameter, the length of Kolmogorov $L_K$ being equal to 24 μm. A control test corresponding to the use of a spinner flask of 0.1 L comprising 50 mL of liquid medium (5), under an agitation of 34 RPM performed by a blade of 3.8 cm in diameter, the length of Kolmogorov $L_K$ being equal to 181 μm, leads to the production of about 1400 extracellular vesicles per producer cell in three hours.

The results of FIGS. 2 and 3 illustrate that, regardless of the type of container (4), when the length of Kolmogorov obtained by stirring the liquid medium (5) is between 5 and 50 μm, preferably between 10 μm and 41 μm, for example 11.4 μm, 13.8 μm, 17 μm, 23 μm, 24 μm, 35 μm and 41 μm, extracellular vesicles are produced by the producer cells suspended in the liquid medium (5). Moreover, as the Kolmogorov length decreases, the number of extracellular vesicles produced per producing cell increases.

Figure 4:
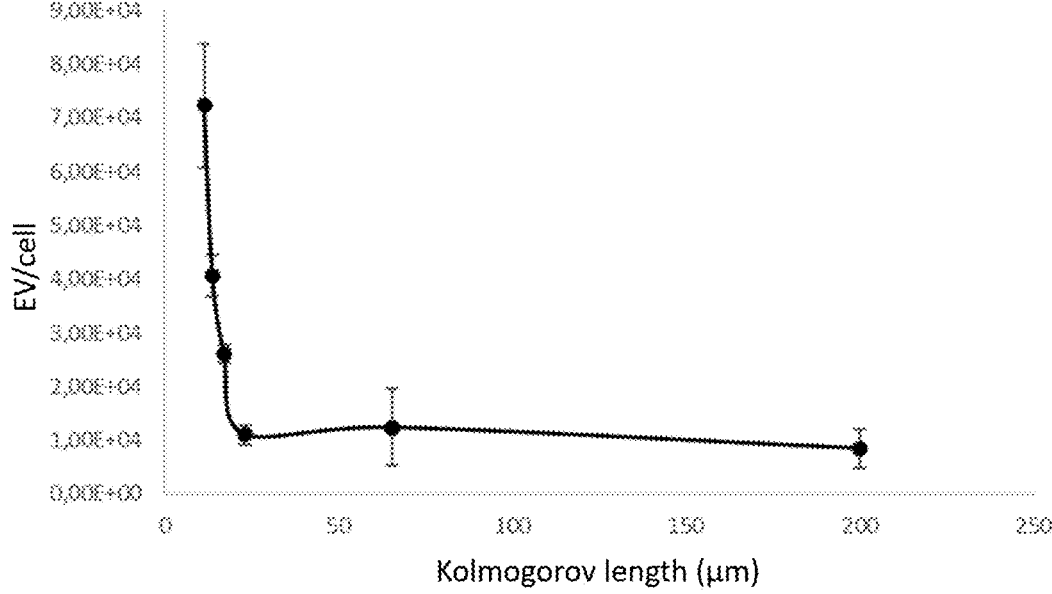
FIG. 4 illustrates the number of extracellular vesicles produced by THP1 cells in a fluidic system after 20 minutes of stirring for different Kolmogorov lengths.

FIG. 4 illustrates the number of extracellular vesicles (EV) produced in a fluidic system (1) for different lengths of Kolmogorov controlled by the agitator (7). The extracellular vesicles (EV) are produced from THP1-type producer cells (6) in the container (4) using a concentration of 100,000,000 suspended cells (6) in 400 mL of liquid medium (5) in a 1000 mL spinner flask. The abscissa corresponds to the length $L_K$ driven by the agitator (7) during the production of extracellular vesicles (EV), calculated by formulae (I), (II) and (III). Significantly high production of extracellular vesicles (EV) is observable by controlling a flow of liquid medium (5) in which the length $L_K$ is less than 17 μm relative to the production of extracellular vesicles (EV) under lower stirring conditions. The yield of production of extracellular vesicles (EV) per producer cell is greater when the length $L_K$ is less than or equal to 50 μm compared to longer $L_K$ lengths, in particular greater than 100 μm.

Figures 5, 6:
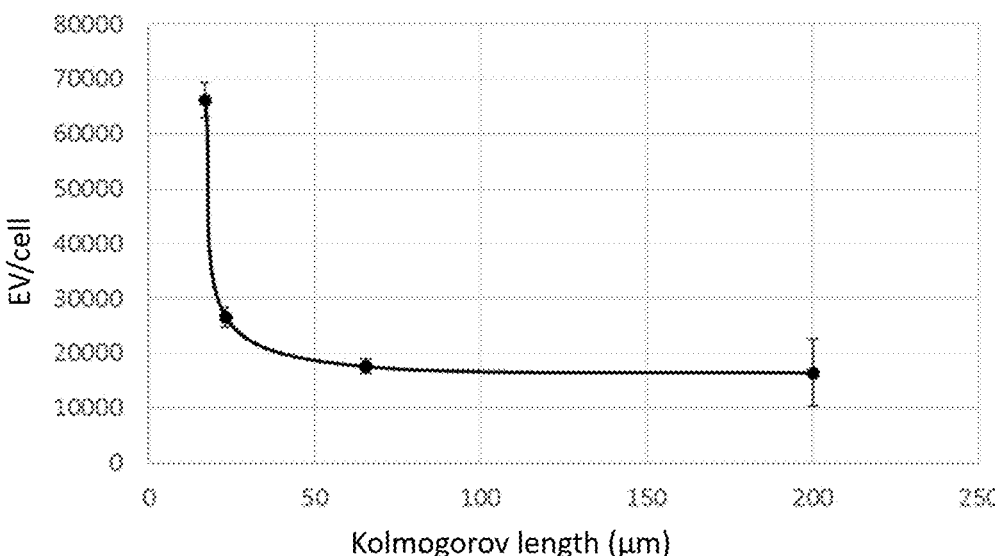
FIG. 5 illustrates the number of extracellular vesicles produced by THP1 cells in a fluidic system for 200 RPM and 300 RPM agitations as a function of time.
FIG. 6 illustrates the number of extracellular vesicles produced by C3H/10T1/2 cells in a fluidic system after 20 minutes of stirring for different Kolmogorov lengths.

FIG. 5 illustrates the number of extracellular vesicles produced per cell as a function of time, by human THP-1 producer cells (6) in a fluidic system by controlling the flow of the liquid medium (5) at agitations of 200 RPM and 300 RPM. The conditions used are 100,000,000 cells in 400 mL in a 1000 mL spinner flask, with a blade of diameter 10.8 cm. The lengths $L_K$ calculated by formulae (I), (II) and (III) are respectively 23 μm (for 300 RPM) and 17 μm (for 400 RPM). The number of extracellular vesicles (EV) produced is much higher for a flow characterized by a length $L_K$ of 17 μm than by a length $L_K$ of 23 μm.

FIG. 6 illustrates the number of extracellular vesicles produced by C3H/10T1/2 producer cells (mouse derived mesenchymal stem cells) in a fluidic system for different Kolmogorov lengths controlled by the agitator (7). A concentration of 100,000,000 producer cells (6) in 400 mL of liquid medium (5) in a 1000 mL spinner flask was used. The abscissa corresponds to the length $L_K$ driven by the agitator (7) during the production of extracellular vesicles EV, calculated by formulae (I), (II) and (III). The production of vesicles per cell increases significantly by controlling a flow of liquid medium (5) in which the length $L_K$ is 17 μm relative to the production of extracellular vesicles (EV) under lower stirring conditions. The yield of production of extracellular vesicles (EV) per producer cell is greater when the length $L_K$ is less than or equal to 50 μm compared to longer $L_K$ lengths, in particular greater than 100 μm from which a plateau in EV/cell yield is reached.

Figures 7, 8:
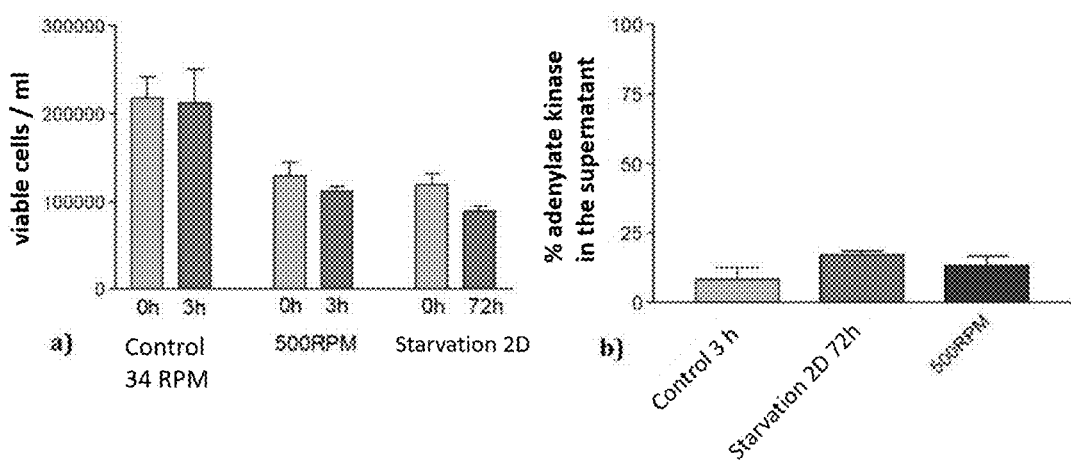
FIG. 7 illustrates the number of extracellular vesicles produced by Raji cells and HeLa cells either in a fluidic system after 3 hours of turbulent agitation (for HeLa cells the agitation is 250 RPM and Kolmogorov length of 41 µm and for Raji cells the agitation is 500 RPM and Kolmogorov length is 24 µm) or in starvation conditions.
FIG. 8 illustrates in 8a) the number of viable Raji cells before and after either a turbulent agitation of 3 hours (500 RPM with Kolmogorov length of 24 µm), or conditions of starvation. In 8b) is illustrated the percentage of adenylate kinase in the supernatant of the control test, of the test in 2D starvation 72 h and of the test according to the invention.

FIG. 7 illustrates first the number of vesicles produced in three hours by Raji-type producer cells (6) on the one hand according to the prior art method of 2D starvation 72 h and, on the other hand, in a fluidic system (1) whose container (4) is a spinner flask with a capacity of 100 mL, the liquid medium (5) is 50 mL, the diameter of the blade is 3.8 cm, the agitation is 500 RPM and the length of Kolmogorov $L_K$ is 24 μm. Secondly, this figure illustrates the number of extracellular vesicles produced in three hours by HeLa-type producer cells (6) on the one hand according to the prior art method of 3D starvation 72 h and, on the other hand, in a fluidic system (1) whose container (4) is a spinner flask with a capacity of 100 mL, the liquid medium (5) is 50 mL, the diameter of the blade is 3.8 cm, the agitation is 250 RPM and the length of Kolmogorov $L_K$ is 41 μm.

This figure illustrates that production of extracellular vesicles in a fluidic system according to the present invention and according to the method of the present invention enables production of extracellular vesicles in much greater quantity and less time than the prior art. Moreover, this figure illustrates that any type of producer cells can be used to produce extracellular vesicles in a fluidic system according to the present invention and according to the method according to the present invention.

FIG. 8a) illustrates the number of viable Raji-type suspended producer cells over time, either after 72 hours in conventional flasks in the liquid medium (5) without agitation (conditions called 2D starvation or 2D starvation 72 h in the present application), or after 3 hours in the presence of turbulent agitation in a fluidic system according to the invention. The fluidic system according to the invention which is used in this figure is a 100 mL spinner flask comprising a liquid medium (5) of 50 mL, a diameter of the blade of 3.8 cm, a stirring of 500 RPM and a length of Kolmogorov $L_K$ of 24 μm. A control test is carried out and corresponds to a 100 mL spinner flask comprising a liquid medium (5) of 50 mL, a diameter of the blade of 3.8 cm, a stirring of 34 RPM and a length of Kolmogorov $L_K$ of 181 μm. The cellular concentrations and viability are measured by NucleoCounter® (NC200™ marketed by the company Chemometec) at times t=0 h and either t=3 h or t=72 h.

The results obtained demonstrate that the number of producer cells does not significantly decrease during turbulent agitation according to the invention, the producer cells resist shear stresses.

FIG. 8b) illustrates the percentage of adenylate kinase in the supernatant between the control test, the 2D starvation 72 h test and the test according to the invention. The adenylate kinase is dosed in the supernatant at times t=0 h and either t=3 h or t=72 h to measure the integrity of the membranes by means of ToxiLight® Assay kit marketed by the company Lonza; the positive control (100% lysis) is carried out with 0.3% by volume of Triton® X-100 relative to the volume of the liquid medium of the control.

It appears that the concentration of adenylate kinase in the supernatant does not vary significantly between the various tests, which demonstrates the absence of cells damage and in particular the maintenance of the integrity of their cellular membranes despite the shearing.

Figure 9:
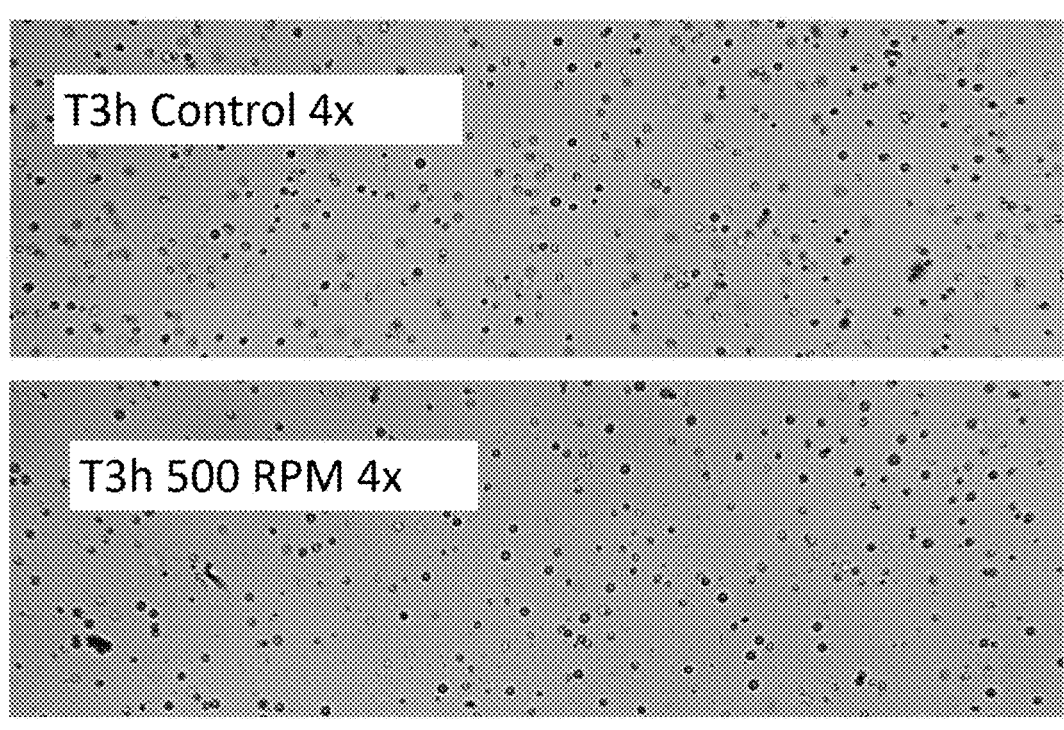
FIG. 9 illustrates the appearance of Raji-producer cells between after 3 hours in the control test and after 3 hours of turbulent agitation (500 RPM with Kolmogorov length of 24 µm), by observation with the optical microscope.

In addition, FIG. 9 illustrates the appearance of the Raji-type producer cells after 3 hours in the test and after 3 hours in the fluidic system according to the invention (the control tests and the tests according to the invention are the same as those in FIG. 8), by observation with an optical microscope at ×4 magnification. These images illustrate the fact that even after the action of the turbulence, there is little or no damage to the producer cells, maintenance of the integrity of the cells and identity of their appearance with the cells of the control test.

Figure 10:
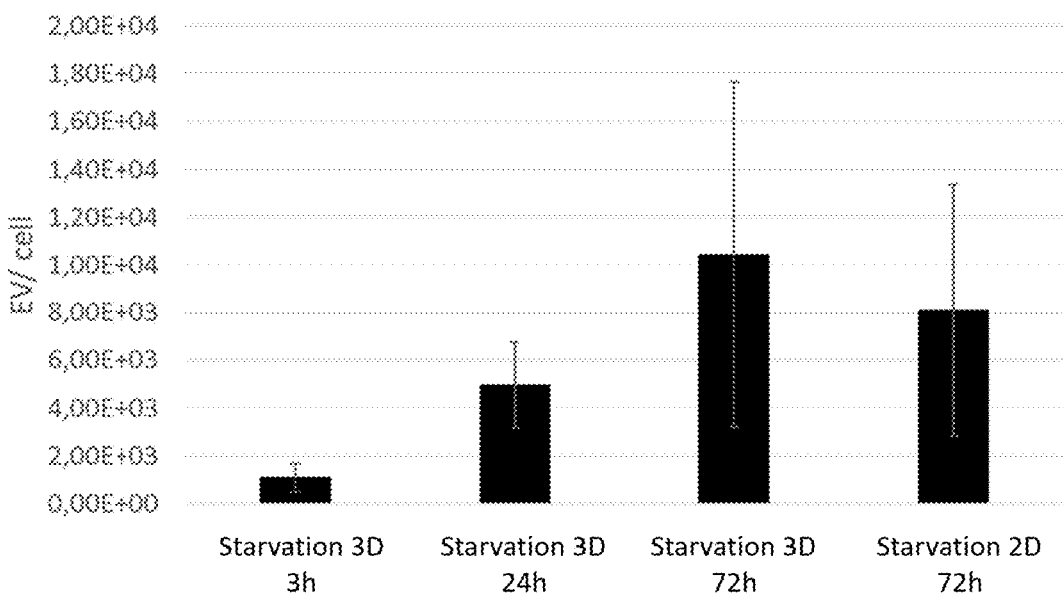
FIG. 10 illustrates the number of extracellular vesicles produced by THP-1 cells in 3D starvation or in 2D starvation for different times.

FIG. 10 illustrates the number of extracellular vesicles produced by human THP-1 cells in conventional flasks in the liquid medium (5) without stirring for 72 h (referred to as 2D starvation 72 h), and in a fluidic system by controlling a flow of the liquid medium (5) in which the length $L_K$ is greater than 200 μm (called 3D starvation). These conditions are the conventional conditions for the production of extracellular vesicles EV. The production of extracellular vesicles (EV) from cells under these different conditions is significantly lower than the production in a flow where the length $L_k$ is less than 17 μm.

Figure 11:
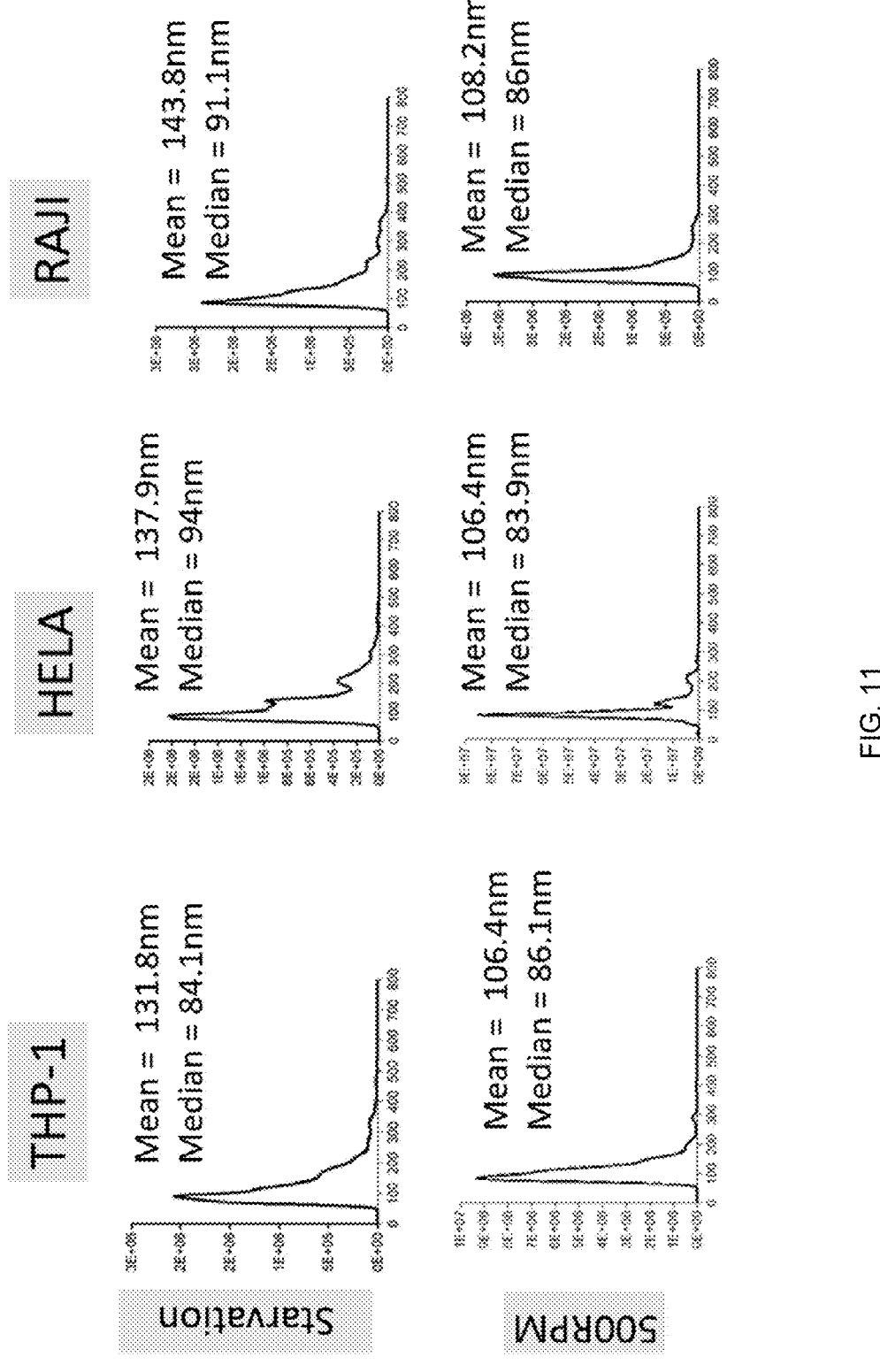
FIG. 11 illustrates the size distribution of extracellular vesicles produced from THP-1, HeLa or Raji producer cells, under conditions of starvation or turbulence (500 RPM with Kolmogorov length of 24 µm), measured by NTA.

FIG. 11 illustrates the size distribution of extracellular vesicles, produced from THP-1, HeLa or Raji producer cells, under conditions of starvation or turbulence by stirring at a speed of 500 RPM. To establish these distributions, the supernatants of the various tests are taken homogeneously and centrifuged 5 min at 2000 G, then the concentration of vesicles and the particle size distribution are measured by Nanoparticle Tracking Analysis (on the apparatus Nano-Sight NS300 sold by the company Malvern Panalytical). These results illustrate that the mean and median diameters of the extracellular vesicles produced according to the invention are similar to both and with those of the extracellular vesicles produced according to the methods of the prior art (starvation).

Figure 12:
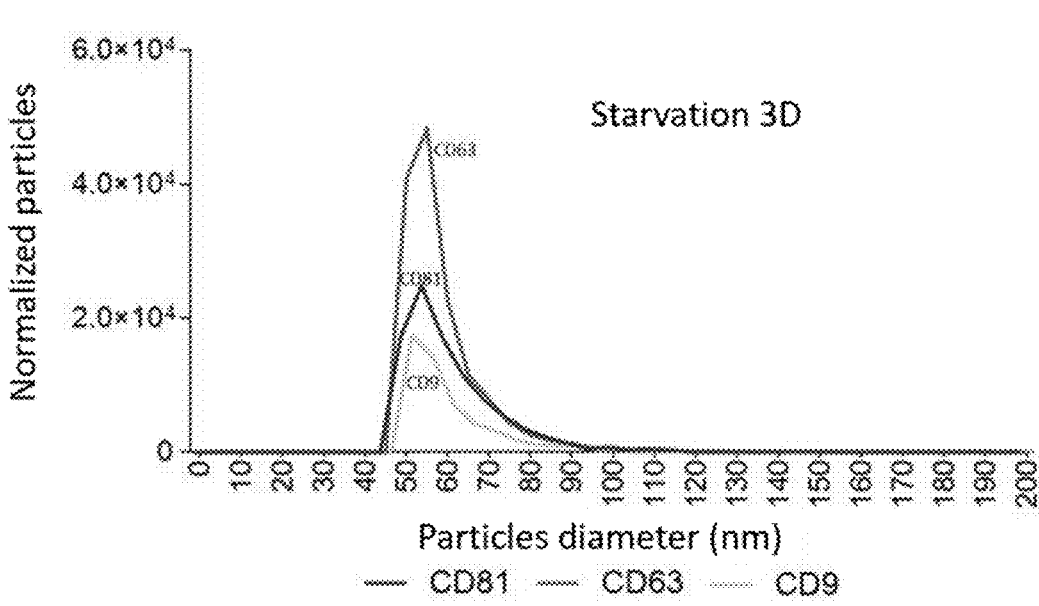
FIG. 12 illustrates the size distribution of extracellular vesicles produced from THP-1 producer cells under conditions of starvation for 72 h or turbulence for 3 hours (500 RPM with Kolmogorov length of 24 µm), measured by Exo View™ R100.
Figure 12:
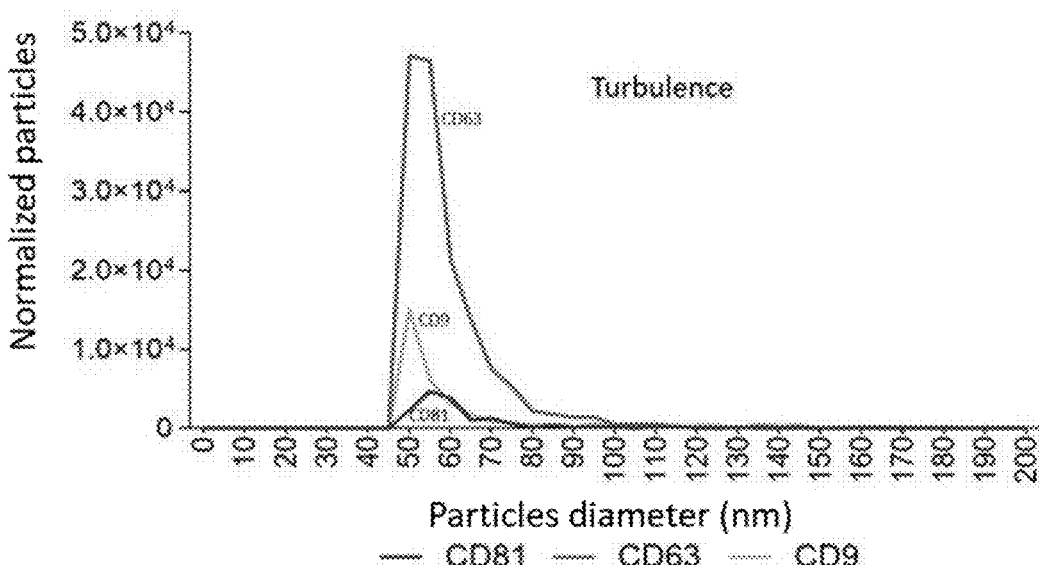
Figure 13:
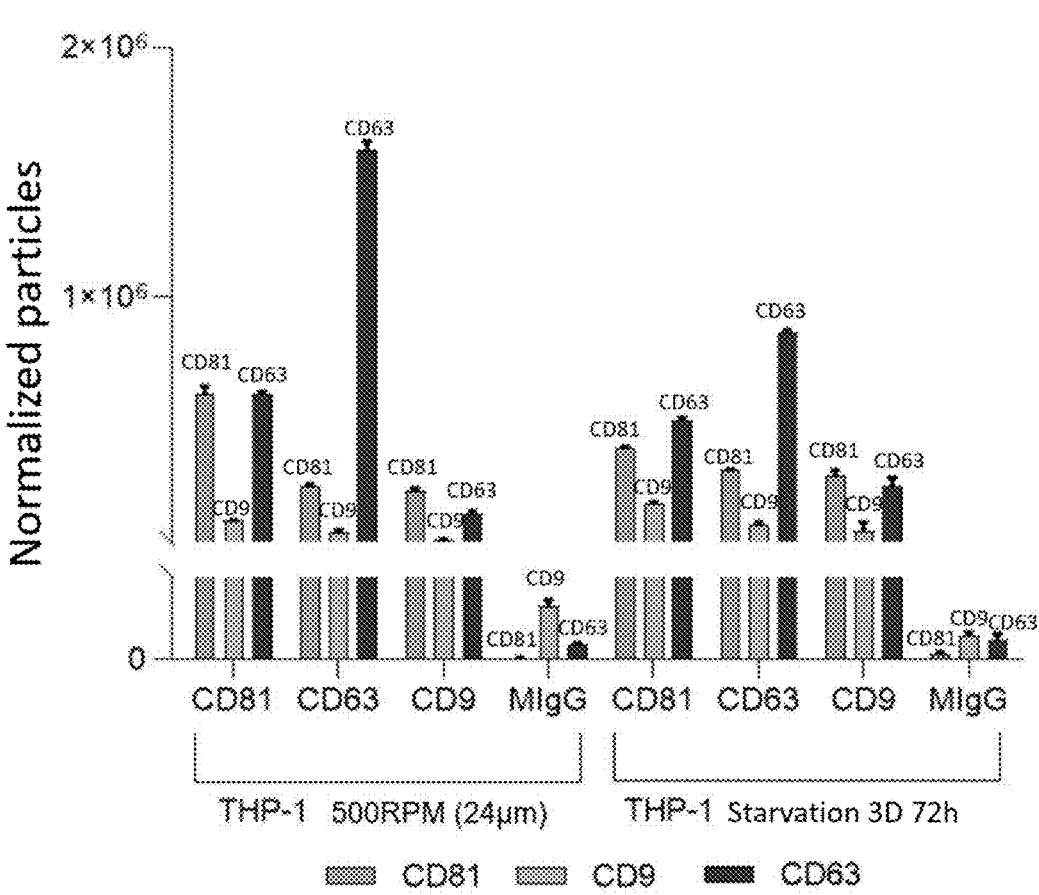
FIG. 13 illustrates the analysis of the membrane markers of extracellular vesicles produced from THP-1 producer cells under conditions of starvation or turbulence (500 RPM with Kolmogorov length of 24 µm), measured by ExoView™ R100.

FIGS. 12 and 13 which follow correspond to the results of analyzing the size distribution of extracellular vesicles and membrane markers of extracellular vesicles. These analyses are carried out by the apparatus ExoView™ R100 marketed by the company NanoView Bioscience. The extracellular vesicles are incubated on a chip containing spots labeled with different antibodies (anti-CD81, anti-CD9, anti-CD63); after washing, anti-CD81 Alexa Fluor® 555, anti-CD9 Alexa Fluor® 647 and anti-CD63 Alexa Fluor® 488 secondary antibodies are added. The collection of the fluorescence and interferometry images makes it possible to obtain the measurements of the sizes and concentrations of the extracellular vesicles in the liquid medium.

FIG. 12 illustrates the size distribution of extracellular vesicles produced according to the invention for 3 hours (turbulence) or according to the 3D starvation method for 72 hours, in both cases from THP1-type producer cells. The extracellular vesicles produced according to the invention are produced from THP1-type producer cells in a 100 mL spinner flask, a liquid medium (5) of 50 mL, a stirring speed of 500 RPM, a length of Kolmogorov $L_k$ of 24 μm and a diameter of the blade of 3.8 cm. The extracellular vesicles produced according to the 3D starvation method 72 h are produced from THP1-type producer cells in a 100 mL spinner flask, a 50 mL liquid medium, a stirring speed of 34 RPM, a length of Kolmogorov $L_k$ of 181 μm and a diameter of the blade of 3.8 cm. The results give values of average diameters of the extracellular vesicles less than those given in FIG. 11, because the analysis method is not the same (measurement by NTA in FIG. 11, which does not allow the detection of the extracellular vesicles of small size, versus measurement by ExoView™ R100 in FIG. 12). The results obtained in FIG. 12 by ExoView™ R100 relate to the analysis of vesicles that attach to anti-CD9, CD63 and CD81 capture antibodies.

The results obtained are as follows:

TABLE 1

| Membrane markers | Mean diameter of extracellular vesicles produced as a function of conditions | |
| --- | --- | --- |
| | Starvation 3D | Turbulence ($L_k$ = 24 μm) |
| CD81 | 62.6 nm | 63.6 nm |
| CD63 | 59.0 nm | 59.8 nm |
| CD9 | 59.9 nm | 60.9 nm |

These results illustrate, on the one hand, that the average diameters of the extracellular vesicles produced according to the invention or according to the 3D starvation method are identical and, on the other hand, the distribution of the membrane markers is not the same as a function of the method for producing the extracellular vesicles (i.e. according to the invention or according to the method of 3D starvation).

FIG. 13 illustrates the analysis of the membrane markers of two types of extracellular vesicles:

extracellular vesicles produced from THP-1 type producer cells in a 100 mL spinner flask, a liquid medium (5) of 50 mL, a stirring speed of 500 RPM and a Kolmogorov length of 24 μm, for 3 hours; and extracellular vesicles produced from producer cells of the THP-1 type in 3D starvation 72 h.

The two types of extracellular vesicles are analyzed with ExoView™ R100 in the following manner: the vesicles are captured by antibodies (anti-CD9, anti-CD63, anti-CD81) on a chip, where the spots of each antibody are separated. Then, the captured vesicles are incubated with a secondary antibody (anti-CD9, anti-CD63, anti-CD81 also) associated with a fluorophore, thereby making it possible to co-locate these markers. On the graph, the capture antibodies are shown on the abscissa axis while the three different columns per abscissa point represent the fluorescent secondary antibodies. Thus, for the CD81 capture antibody, all the captured vesicles should be labeled with the Alexa Fluor® 555fluorophore, except if there is no more epitope available.

The results show, on the one hand, that the typical membrane markers of extracellular vesicles, namely CD81 and CD63 essentially, are present on the extracellular vesicles produced in the presence of a length of Kolmogorov of 24 μm. This demonstrates that the particles produced by the method according to the invention are indeed extracellular vesicles, and that they have markers specific to their parent producer cells.

On the other hand, these results show that for vesicles produced at 500 RPM, there are the same number of particles marked by the fluorophores in CD81 and CD63 on the CD81 capture antibody, and approximately half of the vesicles captured by the CD63 capture antibody are labeled with CD81 fluorescence. Therefore, these two membrane markers CD63 and CD81 are present on the extracellular vesicles produced in the presence of a length of Kolmogorov of 24 μm. There is the same trend of presence and significant co-localization of the two CD63 and CD81 membrane markers on the extracellular vesicles produced in 3D starvation, but the relative distributions differ from those of the extracellular vesicles produced in the presence of a length of Kolmogorov of 24 μm.

Figure 14:
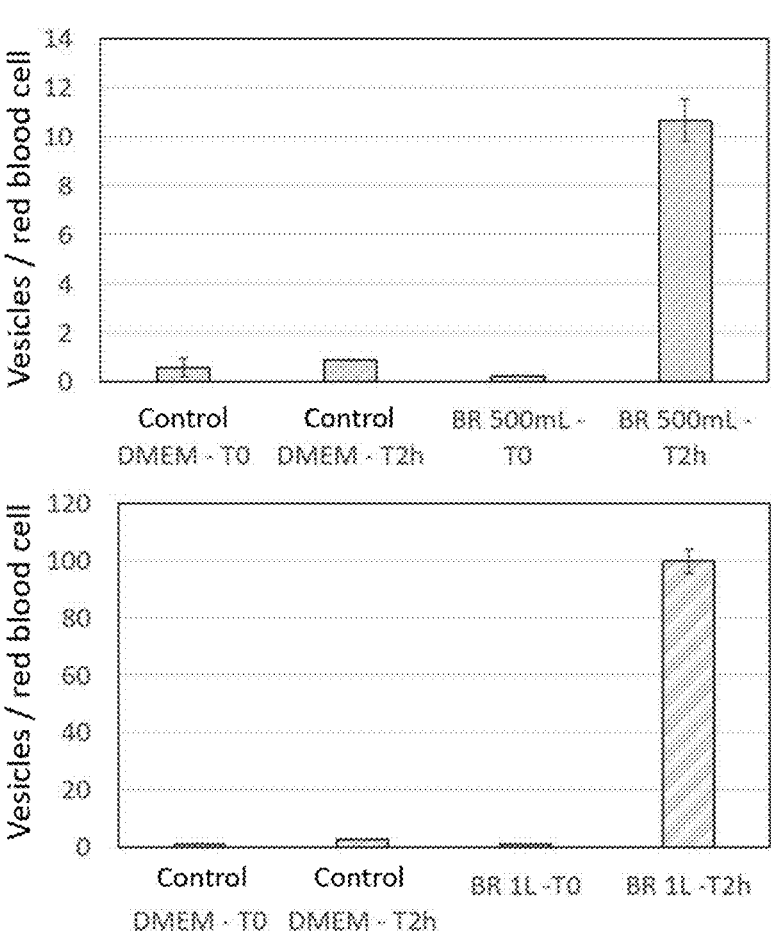
FIG. 14 illustrates the number of extracellular vesicles produced by red blood cells after 2 hours of stirring for different lengths of Kolmogorov (18.6 µm for the figure of the top and 10.9 µm for the figure of the bottom versus a control without agitation)

FIG. 14 illustrates the number of extracellular vesicles produced by red blood cells after 2 hours of stirring for different lengths of Kolmogorov. The count of extracellular vesicles, after 2 hours of stirring (conditions according to the invention: BR 500 mL and BR 1 L) or 2 hours of maintenance without stirring (control condition) is carried out by homogeneous sampling of the supernatants (before experiment and after experiment) and then centrifugation of these supernatants for 5 minutes at 2000G, then measuring the concentration of vesicles by Nanoparticle Tracking Analysis (NanoSight NS300, Malvern Panalytical). The detail of the operating conditions and the results are presented hereinafter.

In a spinner flask of a capacity of 500 mL and having a blade with a diameter of 7.6 cm, $1.5 \times 10^{11}$ red blood cells are introduced into 150 mL of white DMEM. Stirring is carried out at 350 RPM for 2 hours, the length of Kolmogorov $L_K$ being 18.6 µm. Control is carried out in a tube with a screw cap, using $5.1 \times 10^{10}$ red blood cells in 50 mL of white DMEM, this control tube being kept fixed and not being stirred. The results (columns of results BR 500 mL—T0 and BR 500 mL—T2 h) illustrate that agitation of red blood cells at a length of Kolmogorov less than 50 µm such that 18.6 µm results in the production of extracellular vesicles by these red blood cells according to a yield of 10.4 extracellular vesicles by red blood cell.

In a spinner flask of a capacity of 1 L and having a blade with a diameter of 10.8 cm, $1.05 \times 10^{11}$ red blood cells are introduced into 300 mL of white DMEM. Stirring is carried out at 500 RPM for 2 hours, the length of Kolmogorov $L_K$ being 10.9 µm. Control is carried out in a tube with a screw cap, using $1.15 \times 10^{10}$ red blood cells in 50 mL of white DMEM, this control tube being kept fixed and not being stirred. The results (columns of results BR 1 L—T0 and BR 1 L—T2 h) illustrate that agitation of red blood cells at a length of Kolmogorov less than 50 µm such that 10.9 µm results in the production of extracellular vesicles by these red blood cells in a yield of about 100 extracellular vesicles by red blood cell.

Thus, as the stirring speed increases and the Kolmogorov length decreases, the amount of extracellular vesicles produced per red cell increases.

Figure 15:
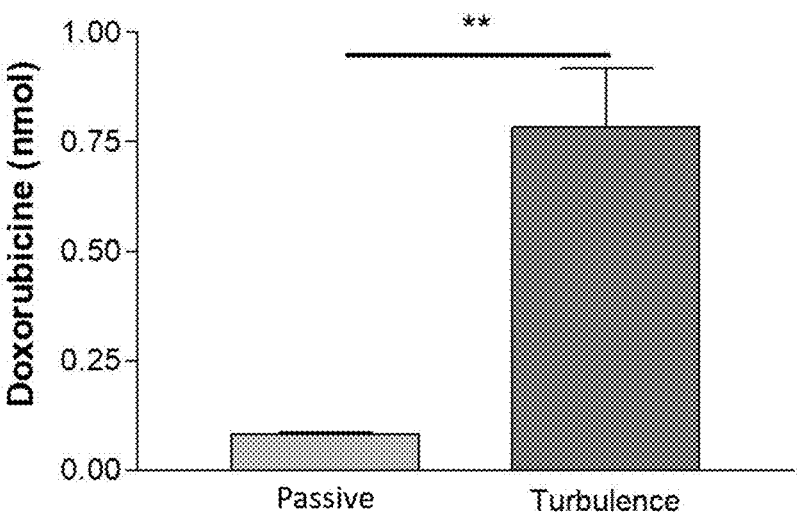
FIG. 15 illustrates the loading of extracellular vesicles with doxorubicin from THP-1 producer cells via passive loading (incubation with 10 µM doxorubicin at 34 RPM with Kolmogorov length of 181 µm for 2 h, followed by washings and then stirring at 2 h at 400 RPM with Kolmogorov length of 28 µm) or via a loading and production in the presence of turbulent stirring (for 2 h at 400 RPM with Kolmogorov length of 28 µm with 10 µM doxorubicin) followed by washes.

FIG. 15 illustrates the loading of extracellular vesicles with doxorubicin in the presence of turbulent agitation.

THP-1 cells are washed and then re-suspended in RPMI in which 1% by volume of penicillin/streptomycin and 10 µM of doxorubicin (Merck) was added. THP-1 cells are introduced into a spinner flask, the liquid medium of which is 50 mL, the concentration of THP-1 cells in the spinner flask being $8.5 \times 10^4$ cells/mL of liquid medium. THP-1 cells are agitated for 2 hours either at 400 RPM, the Kolmogorov length being 28 (doxorubicin internalization condition), either at 34 RPM, the Kolmogorov length being 181 µm (control condition=passive); THP-1 cells are then washed and then again agitated under the same conditions as previously at 400 RPM and Kolmogorov length of 28 µm, in RPMI further comprising 1% by volume penicillin/streptomycin. The samples (including THP-1 cells and extracellular vesicles produced) are then centrifuged 5 minutes at 2000G. The supernatant is ultracentrifuged 1 h30 at 150,000 G, and then the bases of vesicles are re-suspended in PBS (phosphate buffered saline), and lysed with 0.3% Triton® X-100. The fluorescence is measured with a fluorescence spectrophotometer Hitachi F7000 (excitation wavelength: 485 nm, emission wavelength: 560 nm).

The results illustrate that for a number of equal starting cells, the amount of doxorubicin measured in the extracellular vesicles after loading and turbulence production (turbulence condition) is much higher than after a load without turbulence followed by turbulence production (control condition=passive): the doxorubicin loading increases from 0.08 nmol for the fraction containing the extracellular vesicles under the control condition (=passive) to 0.78 nmol for the fraction containing the extracellular vesicles under turbulence condition.

Furthermore, a ratio called purity was determined; it is the ratio of the concentration of extracellular vesicles measured by NTA to the concentration of proteins (in µg/mL). The NTA measurement of the extracellular vesicles concentration is carried out using the following protocol:

homogeneous sampling of the supernatant of the liquid medium of the different conditions for producing extracellular vesicles from THP-1 type producer cells: liquid medium of the conditions of 2D starvation 72 h, liquid medium of 3D starvation 72 h, liquid medium after 3 hours of stirring at 250 RPM, liquid medium after 3 hours of stirring at 500 RPM; then centrifugation for 5 minutes at 2000 G; then measuring the concentration of extracellular vesicles and their distribution in size by Nanoparticle Tracking Analysis (on the apparatus NanoSight NS300 marketed by the company Malvern Panalytical).

The protein concentration measurement is carried out by the Bradford test (ThermoFisher Scientific).

As the protein concentration is measured without lysing the vesicles, the ratio of the extracellular vesicle concentration to the protein concentration (=purity) is considered an indication of the contaminants present in the sample. The results are as follows:

TABLE 2

| | Starvation 2D | Starvation 3D | 250 RPM | 500 RPM |
|---|---|---|---|---|
| THP-1 | $4.83 \times 10^8$ | $9.928 \times 10^8$ | $3.67 \times 10^8$ | $1.15 \times 10^9$ |
| HeLa | N/A | $2.71 \times 10^8$ | $6.74 \times 10^8$ | $6.55 \times 10^8$ |

These results demonstrate that the samples of extracellular vesicles produced according to the invention have a purity similar to that of the samples of extracellular vesicles produced in 2D and 3D starvation. This illustrates that the method for producing extracellular vesicles according to the present invention enables an increase in the amount of extracellular vesicles produced and the production yield of the extracellular vesicles while maintaining the purity level with respect to the methods of the prior art.

The invention claimed is:

1. A method for ex vivo production of extracellular vesicles from suspended producer cells, comprising:

controlling the speed of an agitator adapted for the growth of the suspended producer cells, wherein the producer cells are non-adherent cells or adherent cells detached from a culture support, wherein a container has a shape and dimensions adapted to the generation of a turbulent flow of a liquid medium in the container to exert shear stresses on the producer cells in order to achieve the production of extracellular vesicles, the flow having a Kolmogorov length less than or equal to 50 µm in the container, the container comprising an output, the liquid medium comprising suspended producer cells, and collecting the liquid medium comprising extracellular vesicles at the output of the container.

2. The method according to claim 1 wherein the liquid medium is agitated for at least twenty minutes.

3. The method according to claim 1, wherein a separator depletes part of the liquid medium collected at the output of the container of extracellular vesicle, and wherein the part of the liquid medium is reintroduced into the container.

4. The method according to claim 1, wherein the method comprises a prior step of loading at least one therapeutic and/or imaging agent present in the liquid medium.

5. The method according to claim 1, wherein said flow allows simultaneously charging at least one therapeutic and/or imaging agent into the interior or at the membrane of the producer cells and producing the extracellular vesicles in the container.

6. The method according to claim 1, wherein the flow has a Kolmogorov length less than or equal to 40 μm in the container.

7. Extracellular vesicles obtained by the method for ex vivo production of extracellular vesicles from suspended producer cells according to claim 1.

8. The extracellular vesicles according to claim 7, for their use in immunotherapy, regenerative medicine, alternative or in addition to cell therapy, as a vector for delivering at least one therapeutic agent, and/or in the treatment of tumors, infectious diseases, inflammatory diseases, immunological diseases, metabolic diseases, cancer diseases, genetic diseases, degenerative diseases or diseases secondary to surgery or trauma.

9. A method of treatment in immunotherapy, in regenerative medicine, as an alternative or in addition to cell therapy, as vectors of at least one therapeutic and/or imaging agent, and/or for the treatment of tumors, infectious diseases, inflammatory diseases, immunological diseases, metabolic diseases, cancer diseases, genetic diseases, degenerative diseases or diseases secondary to surgeries or trauma, comprising administering to a subject in need thereof the extracellular vesicles according to claim 7.

* * * * *